US011384081B2

(12) United States Patent
Renno et al.

(10) Patent No.: US 11,384,081 B2
(45) Date of Patent: Jul. 12, 2022

(54) BENZOIMIDAZOLE DERIVATIVES AS ANTICANCER AGENTS

(71) Applicants: CENTRE LEON BERARD, Lyons (FR); HOSPICES CIVILS DE LYON, Lyons (FR); UNIVERSITE CLAUDE BERNARD LYON 1, Villeurbanne (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR)

(72) Inventors: Toufic Renno, Civrieux d'Azergues (FR); Isabelle Coste-Invernizzi, Chazay d'Azergues (FR); Stéphane Giraud, L'Isle d'Abeau (FR); Serge Lebecque, Civrieux d'Azergues (FR)

(73) Assignees: CENTRE LEON BERARD, Lyons (FR); HOSPICES CIVILS DE LYON, Lyons (FR); UNIVERSITE CLAUDE BERNARD LYON 1, Villeurbanne (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 518 days.

(21) Appl. No.: 16/334,513

(22) PCT Filed: Sep. 20, 2017

(86) PCT No.: PCT/EP2017/073801
§ 371 (c)(1),
(2) Date: Mar. 19, 2019

(87) PCT Pub. No.: WO2018/054989
PCT Pub. Date: Mar. 29, 2018

(65) Prior Publication Data
US 2021/0292328 A1 Sep. 23, 2021

(30) Foreign Application Priority Data
Sep. 20, 2016 (EP) .................................. 16306203

(51) Int. Cl.
| C07D 487/04 | (2006.01) |
| A61K 45/06 | (2006.01) |
| C07D 235/18 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 405/12 | (2006.01) |
| C07D 413/12 | (2006.01) |
| C07D 417/12 | (2006.01) |

(52) U.S. Cl.
CPC ............ *C07D 487/04* (2013.01); *A61K 45/06* (2013.01); *C07D 235/18* (2013.01); *C07D 401/04* (2013.01); *C07D 401/12* (2013.01); *C07D 401/14* (2013.01); *C07D 403/04* (2013.01); *C07D 403/12* (2013.01); *C07D 405/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| 6,448,271 | B1 | 9/2002 | Lubisch et al. | |
| 6,759,425 | B2 * | 7/2004 | Sircar | A61K 31/4184 |
| | | | | 514/336 |
| 8,242,284 | B1 | 8/2012 | Gakh et al. | |
| 2014/0128352 | A1 | 5/2014 | Brand et al. | |

FOREIGN PATENT DOCUMENTS

| AU | 5404200 A | 1/2001 |
| JP | 2003-503400 A | 1/2003 |
| WO | WO-98/06703 A1 | 2/1998 |
| WO | WO-03/032984 A1 | 4/2003 |
| WO | WO-2005/030206 A1 | 4/2005 |
| WO | WO-2007/056155 A1 | 5/2007 |
| WO | WO-2008/048991 A2 | 4/2008 |

(Continued)

OTHER PUBLICATIONS

Richards M L et al.: "Substituted 2-phenyl-benzimidazole derivatives: novel compounds that suppress key markers of allergy", European Journal of Medicinal Chemistry, Editions Scientifique ELSEVIER, Paris, FR, vol. 41, No. 8, Aug. 1, 2006, pp. 950-969.

Baldwin, J. J., et al.: "2-Pyridylimidazoles as inhibitors of xanthine oxidase", Journal of Medicinal Chemistry, vol. 20, No. 9, Sep. 1, 1977, pp. 1189-1193.

Keurulainen, L. et al.: "Design and Synthesis of 2-Arylbenzimidazoles and Evaluation of Their Inhibitory Effect against Chlamydia pneumoniae", Journal of Medicinal Chemistry, vol. 53, No. 21, Nov. 11, 2010, pp. 7664-7674.

(Continued)

*Primary Examiner* — Heidi Reese
(74) *Attorney, Agent, or Firm* — Harness, Dickey & Pierce, P.L.C.

(57) ABSTRACT

The disclosure relates to benzoimidazole derivatives, acting as anticancer drugs, as well as pharmaceutical composition containing said compounds. These compounds are able to firstly inhibit the protein/protein interactions of the MAP Kinase Erk, leading to inhibition of proliferation and secondly to induce apoptosis in human cancer cell lines.

15 Claims, 2 Drawing Sheets

(56) References Cited

FOREIGN PATENT DOCUMENTS

| WO | WO-2008/073451 A2 | 6/2008 |
|---|---|---|
| WO | WO-2011/046954 A1 | 4/2011 |
| WO | WO-2012/102937 A2 | 8/2012 |

OTHER PUBLICATIONS

Rios, N. et al.: "Microwave-Assisted Solid-Phase Synthesis of a 1,2-Disubstituted Benzimidazole Library by Using a Phosphonium Linker", Journal of Heterocyclic Chemistry, vol. 50, No. 3, May 1, 2013, pp. 720-726.

Kelly, D. P. et al.: "DNA binding compounds. VI Synthesis and Characterization of 2,5-Disubstituted Bibenzimidazoles Related of the DNA Minor Groove Binder Hoechst 33258", Australian Journal of Chemistry: an International Journal for Chemical Science, vol. 47, No. 9, Jan. 1, 1994, pp. 1751-1769.

Tong, Y. et al.: "Synthesis and Evaluation of a New Generation of Orally Efficacious Benzimidazole-Based Poly(ADP-ribose) Polymerase-1 (PARP-1) Inhibitors as Anticancer Agents", Journal of Medicinal Chemistry, vol. 52, No. 21, Nov. 12, 2009, pp. 6803-6813.

Li, H., et al., "Ligand-Free Pd-Catalyzed Carbonylative Cross-Coupling Reactions inder Atmospheric Pressure of Carbon Monoxide: Synthesis of Aryl Ketones and Heteroaromatic Ketones," Eur. J. Org. Chem. 2011, 14, Mar. 28, 2011, 2662-2667.

Bavetsias, V., et al., "Hit generation and exploration: Imidazo [4,5-b] pyridine derivatives as inhibitors of Aurora Kinases," Bioorganic & Medicinal Chemistry Letters 17 (2007), 12(23) 6567-6571.

Tonelli, M., et al., "Pharmacophore modeling, resistant mutant isolation, docking, and MM-PBSA analysis: Combined Experimental/computer-assisted approach to identify new inhibitors of the bovine viral diarrhea virus (BVDV)," Bioorganic & Medicinal Chemistry, 18 (2010), 2304-2316.

Rzuczek, S., et al., "Studying a Drug-like RNA-Focused Small Molecule Library Identifies Compounds That Inhibit RNA Toxicity in Myotonic Dystrophy," American Chemical Society, ACS Chem, published Sep. 28, 2015.

Chuan-Ming, et al., Fenzi Kexue Xuebao, Journal of Molecular Science, Jun. 2004, 20(2), 35-40.

Chinese Office Action for equivalent Application 2017800702877 (dated Feb. 18, 2022).

Molecule registration No. 1026975-95-0, ChemSpider database (ChemZoo, Inc.) (Jun. 10, 2008).

* cited by examiner

BENZOIMIDAZOLE DERIVATIVES AS ANTICANCER AGENTS

CROSS-REFERENCE TO RELATED APPLICATIONS

This application is a National Phase Entry of International Patent Application No. PCT/EP2017/073801, filed on Sep. 20, 2017, which claims priority to European Patent Application Serial No. 16306203.7, filed on Sep. 20, 2016, both of which are incorporated by reference herein.

BACKGROUND AND SUMMARY

The technical domain of the invention is anticancer drugs.

Chemotherapy, together with surgery and radiotherapy, remains one of the most used approaches for the treatment of cancer. Although some tens of anticancer compounds have been approved for clinical use, there is still a constant need for more selective, more effective and less toxic novel therapeutics. Thus there is an ongoing need in the art to optimize anticancer drugs.

In this context, the invention relates to benzoimidazole derivatives having anticancer properties. The compounds according to the invention are able to firstly inhibit the protein/protein interactions of the MAP Kinase Erk, leading to inhibition of proliferation, and secondly to induce apoptosis of cancer cells, notably as demonstrated in human cancer cell lines of lung, colon, melanoma, sarcoma and pancreatic cancer cell lines, but not of normal cells. The compounds according to the invention are able to inhibit Erk1/2 interaction with MyD88, Erk meaning Extra cellular signal-regulated kinase and MyD88 meaning Myeloid Differentiation primary response gene 88.

Advantageously, the compounds of the invention are also able to stimulate the immunogenic cell death (ICD) via the display of markers like the immunogenic cell death markers. Secretion of ATP, an active process that occurs during ICD, was also induced by the compounds of the invention on the cell membrane notably of mouse lung cells and human colon cells in particular, and of mouse tumor cells. Advantageously, the cell death induced by the compounds of the invention is generally accompanied by the exposure of calreticulin (CRT) on the cell membrane notably of mouse lung cells and human colon cells, and of mouse tumor cells. Indeed, the presence of CRT on the apoptotic cell surface provides an "eat me" signal to macrophages and dendritic cells, leading to the activation of the immune system. Advantageously, the compounds of the invention are able to induce apoptosis by a mechanism distinct from that of kinase inhibitors.

The present invention intends to provide new compounds having one or more of the following characteristics:
- the compounds of the invention are not kinase inhibitors which are known to generally affect multiple molecular targets generating many side effects;
- the compounds of the invention are surprisingly inducers of the immune system;
- the compounds of the invention are safe in vivo at efficient doses;
- the compounds of the invention are less toxic compared to conventional chemotherapy generating less side effects.

One of the purpose of the invention is to provide compounds of formula (I) or (I') as described below, notably for use as a medicament in cancer treatment, as well as the pharmaceutically acceptable salts thereof, stereoisomers or mixtures of stereoisomers thereof, in any proportions, particularly a mixture of enantiomers, and especially a racemic mixture. Another purpose of the invention is to provide a pharmaceutical composition comprising at least one compound of formula (I), (I'), (II) or (III) and a pharmaceutically acceptable carrier. Another purpose of the invention is to provide a method for inhibiting oncogenesis and/or cancer cell growing through the MyD88/ERK cell pathway, in particular for inhibiting the MyD88/ERK interaction, and/or for stimulating the display of immunogenic cell death (ICD) markers on the cell membrane of cancer cells comprising the administration to a person in need thereof of an effective amount of a compound of formula (A) as described below, or a pharmaceutically acceptable salt thereof, a stereoisomer or mixture of stereoisomers thereof, in any proportions, particularly a mixture of enantiomers, and especially a racemic mixture.

Definitions

The term "halogen" or "halo", as used in the present invention, refers to a fluorine, chlorine, bromine or iodine atom.

The term "amino group", as used in the present invention, refers to a group $NH_3$, $NH_2Alk1$ or $NAlk1Alk2$ in which Alk1 and Alk2, identical or different, represent a (C1-C6)-alkyl group as defined below. For example, it can be a dimethylamino group.

The term "(C1-C6)alkyl", as used in the present invention, refers to a straight or branched monovalent saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "(C1-C6)alkylcarbonyl", as used in the present invention, refers to a (C1-C6)alkyl group as defined above bound to the molecule via a —C(=O)— group, including, but not limited to acetyl, propionyl, n-butyryl, sec-butyryl, t-butyryl or iso-propionyl.

The term "oxy(C1-C6)alkylcarbonyl", as used in the present invention, refers to a (C1-C6)alkylcarbonyl group as defined above substituted by at least one oxygen atom, and bound to the molecule via a —C(=O)— group.

The term "(C1-C6)haloalkyl", as used in the present invention, refers to a (C1-C6)alkyl group as defined above substituted by at least one halogen atom, and preferably by at least one chlorine or fluorine atom. It can be in particular a trifluoromethyl group.

The terms "(C1-C6)alkanoic acid amide" as used in the present invention, refers to a (C1-C6)alkyl group as defined above bound to a —C(=O)— group, the carbon of the CO group is bound to a nitrogen atom (NH), the (C1-C6) alkanoic acid amide is bound to the molecule via the alkyl group.

The term "(C1-C6)alkoxy", as used in the present invention, refers to a (C1-C6)alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like.

The term "(C1-C6)alkoxyalkyl", as used in the present invention, refers to (C1-C6)alkoxy group as defined above bound to the molecule via an alkyl group as defined above including, but not limited to $CH_3$—O—$(CH_2)_2$—

The term "(C3-C10)cycloalkyl", as used in the present invention, refers to a hydrocarbon ring having 3 to 10 carbon atoms including, but not limited to, cyclopropyl, cyclopentyl, cyclohexyl and the like.

The term "oxy(C3-C10)cycloalkyl", as used in the present invention, refers to a (C3-C10)cycloalkyl group as defined above substituted by at least one oxygen atom.

The term "aryl", as used in the present invention, refers to an aromatic hydrocarbon group comprising preferably 6 to 10 carbon atoms and comprising one or more fused rings, such as, for example, a phenyl or naphtyl group. Advantageously, it will be a phenyl group.

The term "aryloxy", as used in the present invention, refers to an aryl group as defined above bound to the molecule via an oxygen atom, including, but not limited to phenoxy (Ph-O).

The term "aryloxycarbonyl", as used in the present invention, refers to an aryloxy group as defined above bound to the molecule via a —C(=O)— group, including, but not limited to phenyloxycarbonyl.

The term "arylcarbonyl", as used in the present invention, refers to an aryl group as defined above bound to the molecule via a —C(=O)— group, including, but not limited to phenylcarbonyl.

The term "aryl-(C1-C6)alkyl", as used in the present invention, refers to an aryl group as defined above bound to the molecule via a (C1-C6)alkyl group as defined above. In particular, an aryl-(C1-C6)alkyl group is a benzyl group.

The term "(C1-C6)alkoxyaryl", as used in the present invention, refers to a (C1-C6)alkoxy group as defined above bound to the molecule via an aryl group as defined above. In particular, it can be an methoxyphenyl group ($CH_3$—O-Ph-).

The term "aminoaryl", as used in the present invention, refers to an amino group as defined above bound to the molecule via an aryl group as defined above. In particular, it can be a dimethylaminophenyl group (($CH_3$)$_2$N-Ph-).

The term "haloaryl", as used in the present invention, refers to an aryl group as defined above substituted by at least one halogen atom, and bound to the molecule via the aryl group. In particular, it can be a chlorophenyl group (Cl-Ph-).

The term "oxyaryl", as used in the present invention, refers to an aryl group as defined above substituted by at least one oxygen atom, and bound to the molecule via the aryl group. In particular, it can be a oxophenyl group (O-Ph-).

The term "heteroaryl", as used in the present invention, refers to an aromatic group comprising one or several, notably one or two, preferably one, fused hydrocarbon cycles in which one or several, notably one to four, advantageously one or two, carbon atoms each have been replaced with a heteroatom selected from a sulfur atom, an oxygen atom and a nitrogen atom, preferably selected from an oxygen atom and a nitrogen atom, in particular a nitrogen atom. It can be a benzothiazolyl, furyl, thienyl, pyrrolyl, oxazolyl, isoxazolyl, thiazolyl, isothiazolyl, imidazolyl, pyrazolyl, oxadiazolyl, thiadiazolyl, triazolyl, tetrazolyl, pyridyl, pyridazinyl, pyrimidinyl, pyrazinyl, triazinyl, quinolyl, isoquinolyl, quinoxalyl or indolyl.

The term "(C1-C6)alkoxyheteroaryl", as used in the present invention, refers to a (C1-C6)alkoxy group as defined above bound to the molecule via an heteroaryl group as defined above. In particular, it can be an methoxypyridyl group ($CH_3$—O-pyridyl-).

The term "(C1-C6)alkylheteroaryl", as used in the present invention, refers to a (C1-C6)alkyl group as defined above bound to the molecule via an heteroaryl group as defined above. In particular, it can be an ethylpyridyl ($C_2H_5$-pyridyl-).

The term "aminoheteroaryl", as used in the present invention, refers to an amino group as defined above bound to the molecule via an heteroaryl group as defined above. In particular, it can be an aminopyridyl group ($NH_2$-pyridyl-).

The term "heteroarylcarbonyl", as used in the present invention, refers to an heteroaryl group as defined above bound to the molecule via a —C(=O)— group, including, but not limited to furan.

The term "heterocycle" as used in the present invention refers to a saturated, unsaturated or aromatic, preferably not aromatic such as saturated, monocycle or polycycle (comprising fused, bridged or spiro rings), preferably monocycle comprising preferably 5 to 10, notably 5 or 6, atoms in each ring(s), in which the atoms of the ring(s) consist of carbon atoms and one or more, advantageously 1 to 4, and more advantageously 1 or 2, heteroatoms, such as a nitrogen, oxygen or sulphur atom, the remainder being carbon atoms. A heterocycle can be notably for example thienyl, furanyl, pyrrolyl, pyrrolidinyl, morpholinyl, piperidinyl or piperazinyl, in particular pyrrolidinyl, morpholinyl, piperidinyl or piperazinyl.

The term "(C1-C6)alkylcarbonylheterocycle" as used in the present invention refers to a (C1-C6)alkyl group bound to a carbonyl group, the carbonyl group being bound to the heterocycle, the (C1-C6)alkylcarbonylheterocycle is bound to the molecule via the alkyl group.

The expression "pharmaceutically acceptable" as used in the present invention is intended to mean what is useful to the preparation of a pharmaceutical composition, and what is generally safe and non toxic, for a pharmaceutical use.

The expression "pharmaceutically acceptable salt" is intended to mean, in the framework of the present invention, a salt of a compound which is pharmaceutically acceptable, as defined above, and which possesses the pharmacological activity of the corresponding compound. The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

The term "stereoisomers" as used in the present invention refers to configurational stereoisomers and includes geometric isomers and optical isomers. The geometric isomers, also called E/Z isomers or cis-trans isomers, result from the different position of substituents on a double C=C bond which can have a Z or E configuration, also called cis or trans configuration. The optical isomers result from the different position in space of substituents or lone pair of electrons on an atom (such as a carbon or sulphur atom) comprising four different substituents (including potentially a lone pair of electron). This atom thus represents a chiral or asymmetric center. Optical isomers which are not mirror images of one another are thus designated as "diastereoisomers," and optical isomers which are non-superimposable mirror images are designated as "enantiomers". An equimolar mixture of two enantiomers of a chiral compound is designated as racemate or racemic mixture.

The expression "compound of formula (I)" as used in the present invention includes a compound of formula (Ia), (Ib), (Ic) or (Id).

The expression "compound of formula (I')" as used in the present invention includes a compound of formula (I'a), (I'b), (I'c), (I'd) or (I'e).

The expression "compound of formula (II)" as used in the present invention includes a compound of formula (IIa) or (IIb).

The expression "compound of formula (III)" as used in the present invention includes a compound of formula (IIIa) or (IIIb).

BRIEF DESCRIPTION OF THE DRAWINGS

FIG. 1 represents the fold induction of caspas activity in ordinate and the concentration of compound 2 in μM, from left to right 1 μM, 1.78 μM, 3.16 μM. 5.62 μM, 10 μM, 17.8 μM and 31.6 μM in abscissa.

FIG. 2 represents the fold induction of caspas activity in ordinate and the concentration of compound 6 in μM, from left to right 1 μüM, 1.45 μM, 2.11 μM, 3.08 μM, 4.47 μM, 6.5 μM, 9.46 μM, 13.8 μM and 20 μM in abscissa.

FIG. 3 represents the fold induction of caspas activity in ordinate and the concentration of compound 7 in μM, from left to right 1 μM, 5 μM, 10 μM, 20 μM, 35 μM and 50 μM in abscissa.

FIG. 4 represents the tumor volume in ordinate and the concentration of compound 6 in mg/kg from left to right 50 mg/kg, 25 mg/kg and 12.5 mg/kg.

DETAILED DESCRIPTION

Figure 1:
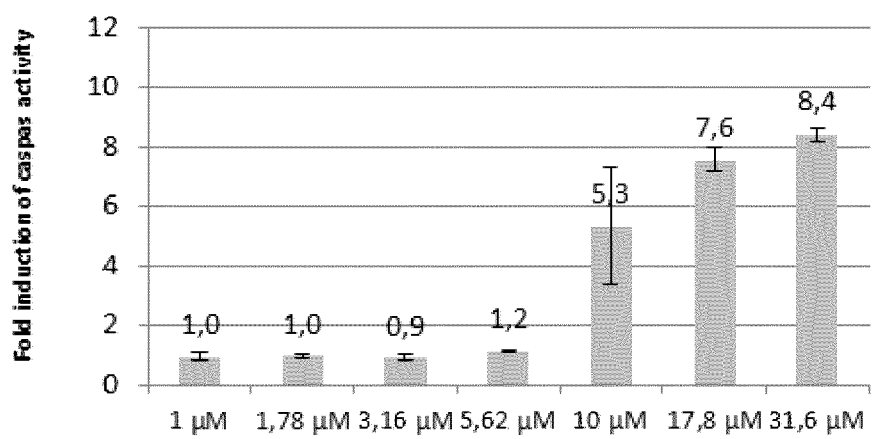
FIGS. 1, 2 and 3 show the induction of apoptosis in HCT116 cells treated with compound 2, 6 and 7 respectively.

The invention relates to a compound of formula (I) below for use as a medicament in a cancer treatment, or a pharmaceutically acceptable salt thereof, a stereoisomer or mixture of stereoisomers thereof, in any proportions, particularly a mixture of enantiomers, and especially a racemic mixture, wherein:
$X_1$, $X_2$ and $X_3$ represent, independently of one another, a carbon atom or a nitrogen atom;
y represents a carbon atom or a sulfur atom;
n represents 0 or 1;
when y represents a sulfur atom then n=0 and $R^3$ does not exist;
$R^1$ represents H, (C1-C6)alkyl or halogen;
when $X_1$ represents a nitrogen atom then $R^2$ does not exist;
when $X_1$ represents a carbon atom then $R^2$ represents H, COOH, (C1-C6)alkyl, (C1-C6)haloalkyl, nitrile (CN), aryl, arylcarbonyl, heteroaryl, CONR11R12, NR13R14, O—(C1-C6)alkyl or SO$_2$NR15R16, COR17; with
R11 represents H or (C1-C6)alkyl;
R12 represents H, (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl or aryl-(C1-C6)alkyl;
R13 represents H or CH$_3$;
R14 represents H, CH$_3$, (C1-C6)alkyl, (C1-C6)alkylcarbonyl, arylcarbonyl, or heteroarylcarbonyl;
R15 represents CH$_3$;
R16 represents CH$_3$;
R17 represents (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl, (C1-C6)alkoxyalkyl or aryl-(C1-C6)alkyl;
$R^3$ represents H, (C1-C6)alkyl or halogen;
$R^4$ represents H, Cl, CN, NO$_2$, NHR18 or OR19 with
R18 represents H, (C1-C6)alkyl, aryl, heteroaryl or (C1-C6)alkylcarbonyl;
R19 represents H or (C1-C6)alkyl;
when $X_2$ represents a nitrogen atom then $R^5$ does not exist;
when $X_2$ represents a carbon atom then $R^5$ represents H, aryl, heteroaryl, heterocycle, aminoheteroaryl, aminoaryl, (C1-C6)alkylcarbonyl, arylcarbonyl, (C1-C6)alkylheteroaryl, heteroarylcarbonyl, (C1-C6)alkoxyarylcarbonyl, oxyaryl, OR20 or NR21R22 with
R20 represents H, (C1-C6)alkyl, aryl, heterocycle, (C1-C6)alkylcarbonylheterocycle or heteroaryl;
R21 represents H or (C1-C6)alkyl, aryl, heteroaryl, (C1-C6)alkyl-N((C1-C6)alkyl)$_2$, (C1-C6)alkyl-NH(C1-C6)alkyl, heteroarylcarbonyl, COR23, (C1-C6)alkylcarbonyl, arylcarbonyl or heteroarylcarbonyl;
R22 represents H, (C1-C6)alkyl, aryl, heteroaryl, (C1-C6)alkyl-N((C1-C6)alkyl)$_2$, (C1-C6)alkyl-NH(C1-C6)alkyl, heteroarylcarbonyl, (C1-C6)alkylheteroaryl, COR23, (C1-C6)alkylcarbonyl, arylcarbonyl or heteroarylcarbonyl;
or R21 and R22 bring together, represent (C3-C10)cycloalkyl or oxy(C3-C10)cycloalkyl;
R23 represents (C1-C6)alkyl, aryl, heteroaryl, (C1-C6)alkylheteroaryl, (C1-C6)alkoxyaryl or (C1-C6)alkyloxyaryl;
when $X_3$ represents a carbon atom then $R^6$ represents H, OH, CH$_3$, (C1-C6)alkoxy or (C1-C6)alkyl;
when $X_3$ represents a nitrogen atom and $X_2$ represents a carbon atom and the cycle including $X_2$, $X_3$ and $R^9$ is saturated with no double bond, then $R^6$ represents a (C1-C6)alkanoic acid amide where the nitrogen atom is substituted by R24 and R25, with R24 and R25 represents independently H, (C1-C6)alkyl, aryl, heteroaryl, heterocycle, (C1-C6)alkoxyaryl, (C1-C6)alkoxyheteroaryl, (C1-C6)alkylcarbonylaryl or (C1-C6)alkylcarbonylheteroaryl;

$R^7$ represents H, N or $CH_3$;

when $R^7$ represents H or $CH_3$ then $R^{10}$ and $R^8$ does not exist;

when $R^7$ represents N, then $R^{10}$ exists and represents a carbon atom, a double bond exists between $R^7$ and $R^{10}$, a single bond exists between $R^{10}$ and $R^9$, a single bond exists between $R^{10}$ and $R^8$ and $R^8$ represents H, (C1-C6)alkyl, halogen;

$R^9$ is a carbon atom.

Any one of the below described embodiments can be combined together, and combined with the compound of formula (I) described above.

According to one particular embodiment of the compound of formula (I) of the invention, the formula (I) is the formula (Ia) below:

(Ia)

According to one particular embodiment of the compound of formula (I) of the invention, the formula (I) is the formula (Ib) below:

(Ib)

According to one particular embodiment of the compound of formula (I) of the invention, the formula (I) is the formula (Ic) below:

(Ic)

According to one particular embodiment of the compound of formula (I) of the invention, the formula (I) is the formula (Id) below:

(Id)

According to a preferred embodiment, the invention relates to a compound of formula (I') below for use as a medicament in a cancer treatment, or a pharmaceutically acceptable salt thereof, a stereoisomer or mixture of stereoisomers thereof, in any proportions, particularly a mixture of enantiomers, and especially a racemic mixture, (I')

wherein:
  $X_1$ represents N or $CR^2$, preferably $CR^2$;
  $X_2$ represents N or $CR^5$, preferably $CR^5$;
  $R^1$ represents H, (C1-C6)alkyl or halogen, preferably H;
  $R^2$ represents H; CN; a (C1-C6)alkyl group optionally substituted with one or several halogen atoms (such as F); an aryl or heteroaryl group optionally substituted with one or more groups selected from halo, (C1-C6) alkyl, OR32 and NR33R34; CONR11R12 or COR17; wherein
    R11 represents H or (C1-C6)alkyl;
    R12 represents a (C1-C6)alkyl, aryl, aryl-(C1-C6)alkyl or 5- or 6-membered heteroaryl group optionally substituted with one or more groups selected from halo, (C1-C6)alkyl, OR35 and NR36R37;
    R17 represents a (C1-C6)alkyl, aryl, aryl-(C1-C6)alkyl or heteroaryl group optionally substituted with one or more groups selected from halo, (C1-C6)alkyl, OR38 and NR39R40;
    R32, R33, R34, R35, R36, R37, R38, R39, and R40 represent, independently of one another, H or (C1-C6)alkyl;
  $R^3$ represents H, (C1-C6)alkyl or halogen, preferably H;
  $R^4$ represents H, Cl, CN, $NO_2$, NHR18 or OR19, preferably H, wherein:
    R18 represents H, (C1-C6)alkyl, aryl, heteroaryl or (C1-C6)alkylcarbonyl;
    R19 represents H or (C1-C6)alkyl;
  $R^5$ represents NR21R22 wherein:
    R21 represents H, R41 or COR41;
    R22 represents H, R42 or COR42;
    or R21 and R22 form together with the nitrogen atom bearing them a heterocycle, preferably a saturated heterocycle, optionally substituted with a (C1-C6) alkyl group;
    R41 and R42 represent, independently of one another, a (C1-C6)alkyl, aryl, aryl-(C1-C6)alkyl or heteroaryl group optionally substituted with one or more groups selected from halo, (C1-C6)alkyl, OR43 and NR44R45;

R43, R44 and R45 represent, independently of one another, H or (C1-C6)alkyl;

R6 represents H, OH, (C1-C6)alkoxy or (C1-C6)alkyl, preferably H; and

R7 represents H or (C1-C6)alkyl, preferably H;

provided that when R2=H, aryl optionally substituted or CONR11R12 with R12=aryl optionally substituted, then R21 represents H or R32 and R22 represents H or R33 or R21 and R22 form together with the nitrogen atom bearing them a heterocycle, preferably a saturated heterocycle, optionally substituted with a (C1-C6)alkyl group.

According to one particular embodiment, the formula (I') is the formula (I'a) below:

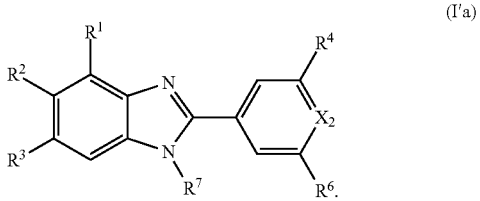

(I'a)

According to one particular embodiment, the formula (I') is the formula (I'b) below:

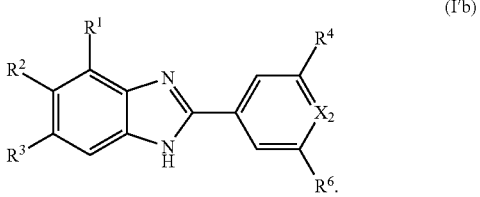

(I'b)

According to one particular embodiment, the formula (I') is the formula (I'c) below:

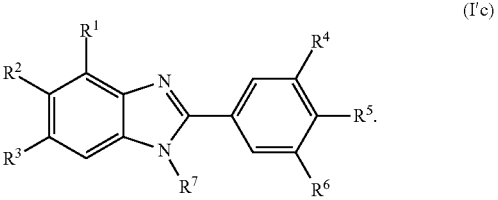

(I'c)

According to one particular embodiment, the formula (I') is the formula (I'd) below:

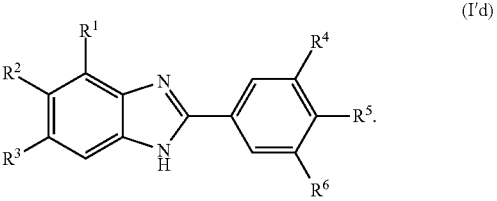

(I'd)

According to one particular embodiment, the formula (I') is the formula (I'e) below:

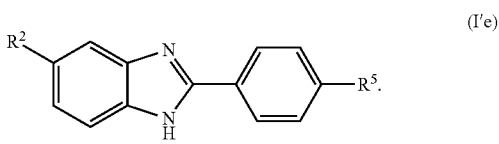

(I'e)

According to one particular embodiment of the compounds of formula (I) or (I') of the invention, $R^1$ is H or (C1-C6)alkyl, such as H or $CH_3$, preferably H. According to one particular embodiment, $X^1$ is a carbon atom for the compounds of formula (I) or $CR^2$ for the compounds of formula (I'). According to one particular embodiment of the compounds of formula (I) or (I') of the invention, $R^2$ is CN. According to another particular embodiment of the compounds of formula (I) or (I') of the invention, $R^2$ is H or a (C1-C6)alkyl group optionally substituted with one or several halogen atoms such as F. $R^2$ can be more particularly H or $CF_3$.

According to another particular embodiment of the compounds of formula (I) or (I') of the invention, $R^2$ is an aryl or heteroaryl group optionally substituted with one or more groups selected from halo, (C1-C6)alkyl, OR32 and NR33R34. Advantageously, it is a heteroaryl group optionally substituted with one or more groups selected from halo, (C1-C6)alkyl, OR32 and NR33R34. The heteroaryl group is preferably a 5- or 6-membered heteroaryl, such as a 6-membered heteroaryl, e.g. pyridyl, pyridazinyl, pyrimidinyl, pyrazinyl, or triazinyl and more particularly pyrimidinyl. $R^2$ can be a pyrimidinyl group.

According to another particular embodiment of the compounds of formula (I) or (I') of the invention, $R^2$ is COR17. Advantageously, R17 represents an aryl, or heteroaryl group, preferably an aryl group, such as a phenyl, optionally substituted with one or more groups selected from halo, (C1-C6)alkyl, OR38 and NR39R40. R17 can be a phenyl.

According to another preferred embodiment of the compounds of formula (I) or (I') of the invention, $R^2$ is CONR11R12, notably with R11 representing H or (C1-C6)alkyl, such as H or $CH_3$, preferably H; and R12 representing a (C1-C6)alkyl, aryl, or 5- or 6-membered heteroaryl group optionally substituted with one or more groups selected from halo, (C1-C6)alkyl, OR35 and NR36R37; such as (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl or aryl-(C1-C6)alkyl.

Advantageously, $R^2$ is CONR11R12 with R11 representing H or (C1-C6)alkyl, such as H or $CH_3$, preferably H, and R12 representing an aryl, or 5- or 6-membered heteroaryl group optionally substituted with one or more groups selected from halo, (C1-C6)alkyl, OR35 and NR36R37; such as aryl, heteroaryl, (C1-C6)alkoxyheteroaryl, (C1-C6) alkoxyaryl, haloaryl, (C1-C6)alkoxyalkyl, (C1-C6)alkylheteroaryl, aminoaryl or aryl-(C1-C6)alkyl. The aryl can be a phenyl and the 5- or 6-membered heteroaryl group can be furyl, thienyl, pyrrolyl, pyridyl, oxazolyl, isoxazolyl, thiazolyle, isothiazolyl, imidazolyl, pyrazolyl, oxadiazolyl, thiadiazolyl, triazolyl, tetrazolyl, pyridazinyl, pyrimidinyl, pyrazinyl, or triazinyl. Preferably, the 5- or 6-membered heteroaryl group is a 6-membered heteroaryl group such as pyridyl, pyridazinyl, pyrimidinyl, pyrazinyl, or triazinyl, preferably a pyridyl.

Advantageously, $R^2$ is CONR11R12 with R11 representing H or (C1-C6)alkyl, such as H or $CH_3$, preferably H, and R12 representing a 5- or 6-membered heteroaryl group optionally substituted with one or more groups selected from halo, (C1-C6)alkyl, OR35 and NR36R37; such as a (C1-C6)alkoxyheteroaryl, (C1-C6)alkylheteroaryl or heteroaryl. The 5- or 6-membered heteroaryl group can be furyl, thienyl, pyrrolyl, pyridyl, oxazolyl, isoxazolyl, thiazolyle, isothiazolyl, imidazolyl, pyrazolyl, oxadiazolyl, thiadiazolyl, triazolyl, tetrazolyl, pyridazinyl, pyrimidinyl, pyrazinyl, or triazinyl. Preferably, the 5- or 6-membered heteroaryl group is a 6-membered heteroaryl group such as pyridyl, pyridazinyl, pyrimidinyl, pyrazinyl, or triazinyl, preferably a pyridyl.

According to one particular embodiment of the compounds of formula (I) or (I') of the invention, $R^2$ is CONR11R12 with R11 representing H or $CH_3$, and R12 representing a pyridyl, an alkoxypyridyl group or an ethylpyridyl. According to one particular embodiment of the compounds of formula (I) or (I') of the invention, $R^3$ is H, Cl or $CH_3$, such as H or $CH_3$, preferably H. According to one particular embodiment of the compounds of formula (I) of the invention, y represents a carbon atom and n is equal to 1, the remaining other chemical groups of the compound of formula (I) are as defined above, including their variants.

According to one particular embodiment of the compounds of formula (I) of the invention, $X^3$ is a carbon atom, the remaining other chemical groups of the compounds of formula (I) are as defined above, including their variants. According to one particular embodiment of the compounds of formula (I) of the invention, $X^2$ is a carbon atom, the remaining other chemical groups of the compounds of formula (I) are as defined above, including their variants.

According to one particular embodiment of the compounds of formula (I) or (I') of the invention, $R^5$ represents NR21R22 with
R21 representing H or (C1-C6)alkyl; and
R22 representing H, (C1-C6)alkyl, aryl, heteroaryl, (C1-C6)alkyl-N((C1-C6)alkyl)$_2$, (C1-C6)alkyl-NH(C1-C6)alkyl, heteroarylcarbonyl, COR23, (C1-C6)alkylcarbonyl, arylcarbonyl or heteroarylcarbonyl.

According to another preferred embodiment of the compounds of formula (I) or (I') of the invention, $R^5$ represents NR21R22 with R21 representing H or (C1-C6)alkyl, preferably H, and R22 representing COR42. Advantageously, R42 represents an aryl or heteroaryl group optionally substituted with one or more groups selected from halo, (C1-C6)alkyl, OR43 and NR44R45. Preferably, the aryl is a phenyl and the heteroaryl is a 5- or 6-membered heteroaryl, more particularly a 5-membered heteroaryl, such as furyl, thienyl, pyrrolyl, oxazolyl, isoxazolyl, thiazolyl, isothiazolyl, imidazolyl, pyrazolyl, oxadiazolyl, thiadiazolyl, triazolyl, or tetrazolyl; in particular furyl, pyrrolyl, oxazolyl, isoxazolyl, imidazolyl, pyrazolyl, oxadiazolyl (such as 1,3,5-oxadiazolyl), triazolyl, or tetrazolyl.

According to another preferred embodiment of the compounds of formula (I) or (I') of the invention, $R^5$ represents NR21R22 with R21 representing H or R41 and R22 representing H or R42 or R21 and R22 form together with the nitrogen atom bearing them a heterocycle, preferably a saturated heterocycle, optionally substituted with a (C1-C6)alkyl group. In particular, $R^5$ represents NR21R22 with R21 representing H or R41 and R22 representing H or R42. Advantageously, R41 and R42 represent, independently of one another, a (C1-C6)alkyl group. The heterocycle is advantageously a saturated 5- or 6-membered heterocycle, such as pyrrolidinyl, morpholinyl, piperidinyl or piperazinyl.

Preferably, $R^5$ represents NR21R22 with R21 and R22 each representing, independently of one another, H, or (C1-C6)alkyl, such as H or $CH_3$. According to one particular embodiment of the compounds of formula (I) or (I') of the invention, $R^6$ represents H or (C1-C6)alkyl, such as H or $CH_3$, preferably H. According to one particular embodiment of the compounds of formula (I) or (I') of the invention, $R^4$ represents H, or (C1-C6)alkyl, such as H or $CH_3$, preferably H.

Advantageously, $R^7$ represents H or $CH_3$, preferably H. Advantageously, for the compounds of formula (I) of the invention, $R^7$ represents H or $CH_3$, in particular H, and $R^{10}$ and $R^8$ do not exist, the remaining other chemical groups of the compound of formula (I) are as defined above, including their variants.

Advantageously, for the compounds of formula (I), $R^7$ represents H, $R^{10}$ and $R^8$ do not exist, $X^2$ and $X^3$ are carbon atoms, $R^6$ is H and $R^5$ represents NR21R22 with
R21 represents H or (C1-C6)alkyl;
R22 represents H, (C1-C6)alkyl, aryl, heteroaryl, (C1-C6)alkyl-N((C1-C6)alkyl)$_2$, (C1-C6)alkyl-NH(C1-C6)alkyl, heteroarylcarbonyl, COR23, (C1-C6)alkylcarbonyl, arylcarbonyl or heteroarylcarbonyl;
the remaining other chemical groups of the compound of formula (I) are as defined above, including their variants.

Advantageously, for the compounds of formula (I), $R^7$ represents H, $R^{10}$ and $R^8$ do not exist, $X^2$ and $X^3$ are carbon atoms, $R^6$ is H and $R^5$ represents NR21R22 with
R21 represents H or $CH_3$;
R22 represents H, or $CH_3$;
the remaining other chemical groups of the compound of formula (I) are as defined above, including their variants.

It is understood, that any one of the above described embodiments can be combined together, with any one of another embodiment of the list. For example, it could be envisaged to combine a selection made from the list describing $R^2$, either from the whole list or part of the list, with any one of the other embodiment of another list, like for example $R^5$, either from the whole list or part of the list of $R^5$. Advantageously, for the compounds of formula (I), $R^1$ represents H, $R^2$ represents CONR11R12, $X^1$ is a carbon atom, n is 1, $R^3$ represents H and y is a carbon atom, the remaining other chemical groups of the compound of formula (I) are as defined above, including their variants.

According to a first preferred embodiment of the compounds of formula (I) or (I') of the invention:
$R^2$ is CONR11R12 with R11 representing H or (C1-C6)alkyl, such as H or $CH_3$, preferably H, and R12 representing a 5- or 6-membered heteroaryl group optionally substituted with one or more groups selected from halo, (C1-C6)alkyl, OR35 and NR36R37; and
$R^5$ is NR21R22 with R21 representing H or R41 and R22 representing H or R42 or R21 and R22 form together with the nitrogen atom bearing them a heterocycle, preferably a saturated heterocycle, optionally substituted with a (C1-C6)alkyl group.

According to a second preferred embodiment of the compounds of formula (I) or (I') of the invention:
$R^2$ is CONR11R12 with R11 representing H or (C1-C6)alkyl, such as H or $CH_3$, preferably H, and R12 representing a 5- or 6-membered heteroaryl group optionally substituted with one or more groups selected from halo, (C1-C6)alkyl, OR35 and NR36R37; and
$R^5$ is NR21R22 with R21 representing H or R41 and R22 representing H or R42.

According to a third preferred embodiment of the compounds of formula (I) or (I') of the invention:

R² is CONR11R12 with R11 representing H or (C1-C6) alkyl, such as H or CH₃, preferably H, and R12 representing a 5- or 6-membered heteroaryl group optionally substituted with one or more groups selected from halo, (C1-C6)alkyl, OR35 and NR36R37; and R⁵ is NR21R22 with R21 and R22 each representing, independently of one another, H, or (C1-C6)alkyl, such as H or CH₃.

According to a fourth preferred embodiment of the compounds of formula (I) or (I') of the invention:

R² is CONR11R12 with R11 representing H and R12 representing a pyridyl group optionally substituted with one or more groups selected from halo, (C1-C6)alkyl, OR35 and NR36R37; and R⁵ is NR21R22 with R21 and R22 each representing, independently of one another, H, or (C1-C6)alkyl, such as H or CH₃.

In the above-mentioned four preferred embodiments, R¹, R³, R⁴, R⁶ and R⁷ each represent advantageously H. In the above-mentioned four preferred embodiments, the 5- or 6-membered heteroaryl group can be furyl, thienyl, pyrrolyl, pyridyl, oxazolyl, isoxazolyl, thiazolyle, isothiazolyl, imidazolyl, pyrazolyl, oxadiazolyl, thiadiazolyl, triazolyl, tetrazolyl, pyridazinyl, pyrimidinyl, pyrazinyl, or triazinyl. Preferably, the 5- or 6-membered heteroaryl group is a 6-membered heteroaryl group such as pyridyl, pyridazinyl, pyrimidinyl, pyrazinyl, or triazinyl, preferably a pyridyl.

Advantageously the compound of formula (I) or (I') is chosen among compounds 1 to 46, preferably compounds 1 to 3, 5 to 10, 12 to 16, 19, 24 to 26, 28 to 35, 37, 38, 40 to 42, 45 and 46, as disclosed in the examples and the pharmaceutically acceptable salts thereof. Preferably, the compound of formula (I) or (I') is chosen among compounds 2, 6, and 7 as disclosed in the examples and the pharmaceutically acceptable salts thereof.

The invention also relates to a method of treatment of cancer comprising the administration of an effective amount of a compound of formula (I) or (I') or any one of its embodiments disclosed above to a person in need thereof. The invention also relates to the use of a compound of formula (I) or (I') or any one of its embodiments disclosed above for the manufacture of a medicament for the treatment of cancer. The cancer to be treated will be advantageously lung cancer, colon cancer, colorectal cancer head and neck cancer, prostate cancer, breast cancer, ovarian cancer, cervical cancer, leukemia, lymphoid cancer, skin cancer, pancreatic cancer, intestinal cancer, liver cancer, bladder cancer, esophageal cancer, gastric cancer, male genital cancer, mesothelioma, sarcoma or bone cancer.

The present invention relates also to a method for inhibiting oncogenesis and/or cancer cell growing through the MyD88/ERK cell pathway, in particular for inhibiting the MyD88/ERK interaction, and/or for stimulating the display of immunogenic cell death (ICD) markers on the cell membrane of cancer cells comprising the administration to a person in need thereof of an effective amount of a compound of following formula (A), or a pharmaceutically acceptable salt thereof, a stereoisomer or mixture of stereoisomers thereof, in any proportions, particularly a mixture of enantiomers, and especially a racemic mixture:

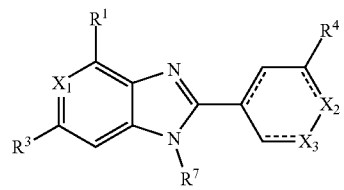

(A)

wherein:
all the bonds ═════ represent a single bond or a double bond (so as to form a saturated or aromatic 6-membered ring);

$X_1$ represents N or $CR^2$, preferably $CR^2$;

$X_2$ represents N or $CR^5$, preferably $CR^5$, when ═════ represents a double bond, or $CHR^5$, preferably $CH_2$, when ═════ represents a single bond;

$X_3$ represents $CR^6$ when ═════ represents a double bond, or $NR^{6a}$ when ═════ represents a single bond;

$R^1$ represents H, (C1-C6)alkyl or halogen, preferably H;

$R^2$ represents H; CN; a (C1-C6)alkyl group optionally substituted with one or several halogen atoms (such as F); an aryl or heteroaryl group optionally substituted with one or more groups selected from halo, (C1-C6) alkyl, OR32 and NR33R34; COOR11; NR11COR12; CONR11R12 or COR17; wherein R11 represents H or (C1-C6)alkyl;

R12 represents H or a (C1-C6)alkyl, aryl, aryl-(C1-C6) alkyl or heteroaryl group optionally substituted with one or more groups selected from halo, (C1-C6) alkyl, OR35 and NR36R37;

R17 represents a (C1-C6)alkyl, aryl, aryl-(C1-C6)alkyl or heteroaryl group optionally substituted with one or more groups selected from halo, (C1-C6)alkyl, OR38 and NR39R40;

R32, R33, R34, R35, R36, R37, R38, R39, and R40 represent, independently of one another, H or (C1-C6)alkyl;

$R^3$ represents H, (C1-C6)alkyl or halogen, preferably H;

$R^4$ represents H, Cl, CN, $NO_2$, NHR18 or OR19, preferably H, wherein:

R18 represents H, (C1-C6)alkyl, aryl, heteroaryl or (C1-C6)alkylcarbonyl;

R19 represents H or (C1-C6)alkyl;

$R^5$ represents H, R46, COR46, OR20 or NR21R22, preferably NR21R22, wherein:

R20 represents H or a (C1-C6)alkyl, aryl, aryl-(C1-C6) alkyl or heteroaryl group optionally substituted with one or more groups selected from halo, (C1-C6) alkyl, OR47, NR48R49 and COR50;

R21 represents H, R41 or COR41;

R22 represents H, R42 or COR42;

or R21 and R22 form together with the nitrogen atom bearing them a heterocycle, preferably a saturated heterocycle, optionally substituted with a (C1-C6) alkyl group;

R41 and R42 represent, independently of one another, a (C1-C6)alkyl, aryl, aryl-(C1-C6)alkyl or heteroaryl group optionally substituted with one or more groups selected from halo, (C1-C6)alkyl, OR43 and NR44R45;

R46 represents a (C1-C6)alkyl, aryl, aryl-(C1-C6)alkyl or heteroaryl group, preferably a heteroaryl group, optionally substituted with one or more groups selected from halo, (C1-C6)alkyl, OR51 and NR52R53;

R43, R44, R45, R47, R48, R49, R51, R52 and R53 represent, independently of one another, H or (C1-C6)alkyl;

R50 represents a (C1-C6)alkyl, aryl, heterocycle or heteroaryl group, preferably a heterocycle group, optionally substituted with one or more groups selected from halo and (C1-C6)alkyl;

$R^6$ represents H, OH, (C1-C6)alkoxy or (C1-C6)alkyl, preferably H;

$R^{6a}$ represents a (C1-C6)alkyl substituted with one CONHR54 group wherein:
R54 represents a (C1-C6)alkyl, aryl, aryl-(C1-C6)alkyl, heterocycle or heteroaryl group, preferably a heterocycle group, optionally substituted with one or more groups selected from halo, (C1-C6)alkyl, OR55, NR56R57 and COR58;
R55, R56 and R57 represent, independently of one another, H or (C1-C6)alkyl;
R58 represents a (C1-C6)alkyl; and $R^7$ represents H or (C1-C6)alkyl, preferably H.

According to one particular embodiment of the compounds of formula (A) of the invention, $R^1$ is H or (C1-C6) alkyl, such as H or $CH_3$, preferably H. According to one particular embodiment of the compounds of formula (A) of the invention, $X^1$ is $CR^2$. According to one particular embodiment of the compounds of formula (A) of the invention, $R^2$ is CN. According to another particular embodiment of the compounds of formula (A) of the invention, $R^2$ is H or a (C1-C6)alkyl group optionally substituted with one or several halogen atoms such as F. $R^2$ can be more particularly H or $CF_3$.

According to another particular embodiment of the compounds of formula (A) of the invention, $R^2$ is NR11COR12. Advantageously, R11 represents H or (C1-C6)alkyl, such as H or $CH_3$, preferably H, and R12 represents an aryl or heteroaryl group, preferably a heteroaryl group, optionally substituted with one or more groups selected from halo, (C1-C6)alkyl, OR35 and NR36R37. The aryl can be a phenyl and the heteroaryl can be a 5- or 6-membered heteroaryl group such as furyl, thienyl, pyrrolyl, pyridyl, oxazolyl, isoxazolyl, thiazolyle, isothiazolyl, imidazolyl, pyrazolyl, oxadiazolyl, thiadiazolyl, triazolyl, tetrazolyl, pyridazinyl, pyrimidinyl, pyrazinyl, or triazinyl.

According to another particular embodiment of the compounds of formula (A) of the invention, $R^2$ is an aryl or heteroaryl group optionally substituted with one or more groups selected from halo, (C1-C6)alkyl, OR32 and NR33R34. Advantageously, it is a heteroaryl group optionally substituted with one or more groups selected from halo, (C1-C6)alkyl, OR32 and NR33R34. The heteroaryl group is preferably a 5- or 6-membered heteroaryl, such as a 6-membered heteroaryl, e.g. pyridyl, pyridazinyl, pyrimidinyl, pyrazinyl, or triazinyl and more particularly pyrimidinyl. $R^2$ can be a pyrimidinyl group.

According to another particular embodiment of the compounds of formula (A) of the invention, $R^2$ is COR17. Advantageously, R17 represents an aryl, or heteroaryl group, preferably an aryl group, such as a phenyl, optionally substituted with one or more groups selected from halo, (C1-C6)alkyl, OR38 and NR39R40. R17 can be a phenyl.

According to another preferred embodiment of the compounds of formula (A) of the invention, $R^2$ is COOR11 or CONR11R12, preferably CONR11R12. Advantageously, R11 represents H or (C1-C6)alkyl, such as H or $CH_3$, preferably H, and R12 represents an aryl or heteroaryl group, preferably a heteroaryl group, optionally substituted with one or more groups selected from halo, (C1-C6)alkyl, OR35 and NR36R37. The aryl can be a phenyl and the heteroaryl can be a 5- or 6-membered heteroaryl group such as furyl, thienyl, pyrrolyl, pyridyl, oxazolyl, isoxazolyl, thiazolyle, isothiazolyl, imidazolyl, pyrazolyl, oxadiazolyl, thiadiazolyl, triazolyl, tetrazolyl, pyridazinyl, pyrimidinyl, pyrazinyl, or triazinyl. Preferably, the heteroaryl group is a 6-membered heteroaryl group such as pyridyl, pyridazinyl, pyrimidinyl, pyrazinyl, or triazinyl, preferably a pyridyl.

According to one particular embodiment of the compounds of formula (A) of the invention, $R^3$ is H, Cl or $CH_3$, such as H or $CH_3$, preferably H. According to one particular embodiment of the compounds of formula (I) or (I') of the invention, $R^4$ represents H, or (C1-C6)alkyl, such as H or $CH_3$, preferably H. According to one particular embodiment of the compounds of formula (A) of the invention, $X^2$ is $CR^5$. Advantageously, $R^5$ represents NR21R22.

According to one preferred embodiment of the compounds of formula (A) of the invention, $R^5$ represents NR21R22 with R21 representing H or (C1-C6)alkyl, preferably H, and R22 representing COR42. Advantageously, R42 represents an aryl or heteroaryl group optionally substituted with one or more groups selected from halo, (C1-C6)alkyl, OR43 and NR44R45. Preferably, the aryl is a phenyl and the heteroaryl is a 5- or 6-membered heteroaryl, more particularly a 5-membered heteroaryl, such as furyl, thienyl, pyrrolyl, oxazolyl, isoxazolyl, thiazolyl, isothiazolyl, imidazolyl, pyrazolyl, oxadiazolyl, thiadiazolyl, triazolyl, or tetrazolyl; in particular furyl, pyrrolyl, oxazolyl, isoxazolyl, imidazolyl, pyrazolyl, oxadiazolyl (such as 1,3,5-oxadiazolyl), triazolyl, or tetrazolyl.

According to another preferred embodiment of the compounds of formula (A) of the invention, $R^5$ represents NR21R22 with R21 representing H or R41 and R22 representing H or R42 or R21 and R22 form together with the nitrogen atom bearing them a heterocycle, preferably a saturated heterocycle, optionally substituted with a (C1-C6) alkyl group. In particular, $R^5$ represents NR21R22 with R21 representing H or R41 and R22 representing H or R42. Advantageously, R41 and R42 represent, independently of one another, a (C1-C6)alkyl group. The heterocycle is advantageously a saturated 5- or 6-membered heterocycle, such as pyrrolidinyl, morpholinyl, piperidinyl or piperazinyl. Preferably, $R^5$ represents NR21R22 with R21 and R22 each representing, independently of one another, H, or (C1-C6)alkyl, such as H or $CH_3$.

According to one particular embodiment of the compounds of formula (A) of the invention, $X^3$ is $CR^6$. Advantageously, $R^6$ represents H or (C1-C6)alkyl, such as H or $CH_3$, preferably H. According to one particular embodiment of the compounds of formula (A) of the invention, $R^7$ represents H or $CH_3$, preferably H. Advantageously, $R^1$, $R^3$, $R^4$, $R^6$ and $R^7$ each represent advantageously H.

It is understood, that any one of the above described embodiments can be combined together, with any one of another embodiment of the list. For example, it could be envisaged to combine a selection made from the list describing $R^2$, either from the whole list or part of the list, with any one of the other embodiment of another list, like for example $R^5$, either from the whole list or part of the list of $R^5$. The compound of formula (A) can be in particular a compound of formula (I') as defined above according to any one of its embodiments disclosed above. Advantageously, the compound of formula (A) is chosen among compounds 1 to 46, preferably compounds 2, 6 and 7, as disclosed in the examples and the pharmaceutically acceptable salts thereof.

The invention relates also to a pharmaceutical composition comprising at least one compound of formula (I) or (I')

as defined above according to any one of their embodiments and a pharmaceutically acceptable carrier. The invention relates also to a pharmaceutical composition comprising at least one compound of formula (II) or (III) as defined below according to any one of their embodiments and a pharmaceutically acceptable carrier. The invention relates also to a pharmaceutical composition comprising at least one compound of formula (I) or (I') as defined above according to any one of their embodiments, said compound of formula (I) or (I') being linked to an antibody, advantageously via a linker, in order to form an ADC. The invention relates also to a pharmaceutical composition comprising at least one compound of formula (II) or (III) as defined below according to any one of their embodiments, said compound of formula (II) or (III) being linked to an antibody, advantageously via a linker, in order to form an ADC.

Pharmaceutical compositions according to the invention may be formulated for parenteral (for example subcutaneous, intraperitoneal, intramuscular, intravenous, intracranial, intrathecal, etc.), oral, sublingual, transdermal, local or rectal administration, intended for mammals, including humans. The dosage varies according to the treatment and according to the condition in question. In the pharmaceutical compositions of the present invention, the active ingredient can be administered in the form of administration units, mixed with conventional pharmaceutical carriers, to animals or human beings.

Appropriate oral administration unit forms include tablets, gels, powders, granules, and oral solutions or suspensions, and parenteral administration forms, notably intraperitoneal. When a solid composition is prepared in the form of tablets, the main active ingredient is mixed with a pharmaceutical carrier such as gelatin, starch, lactose, magnesium stearate, talc, gum arabic, or the like. The tablets can be coated with sucrose or other appropriate materials or even be treated so that they have an extended or delayed activity and that they continuously release a predetermined quantity of active ingredient.

A capsule preparation is obtained by mixing the active ingredient with a diluent and pouring the mixture obtained into hard or soft capsules. A preparation in the form of a syrup or elixir can contain the active ingredient conjointly with a sweetener, an antiseptic and an appropriate taste enhancer and dye. Powders or granules dispersible in water can contain the active ingredient in mixture with dispersing or wetting agents or suspending agents, and with flavor correctors or sweeteners.

For parenteral administration, aqueous suspensions, isotonic saline solutions or sterile and injectable solutions are used that contain pharmacologically-compatible dispersing agents and/or wetting agents. The active ingredient can also be formulated in the form of microcapsules, possibly with one or more additional carriers. Advantageously, the pharmaceutical composition according to the invention further comprises at least one antitumour drug different from the compound of formula (I) or (I') or (II) or (III), as combined preparation for a simultaneous, separate or sequential use in the treatment of mammals, in particular humans, suffering from a cancer such as a malignant (cancerous) tumour.

Advantageously, the pharmaceutical composition according to the invention further comprises at least one of the following antitumour drugs and/or targeted therapies, without being limited to this list:
abraxane, abarelix, aldesleukin, alemtuzumab, alitretinoin, allopurinol, altretamine, anastrozole, arsenic trioxide, asparaginase, azacitidine, atezolizumab, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, ipilimumab, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nivolumab, nofetumomab, oxaliplatin, paclitaxel, pamidronate, panitumumab, pegaspargase, pegfilgrastim, pembrolizumab, pemetrexed disodium, pentostatin, pipobroman, plicamycin, procarbazine, quinacrine, rasburicase, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate as well as immune checkpoint inhibitors including antibodies against PD1 (programmed cell death-1), PD-L1 (programmed cell death-1-ligand 1), and CTLA4 (cytotoxic T-lymphocyte-associated protein 4). The pharmaceutical compositions according to the present invention are useful in the treatment of cancer, notably as defined above.

The invention relates also to a compound of formula (II) below:

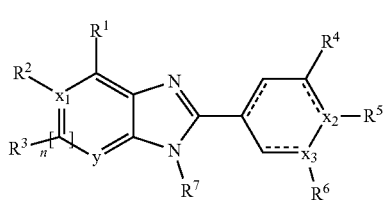

(II)

wherein
  $X_1$, $X_2$ and $X_3$ represents, independently of one another, a carbon atom or a nitrogen atom;
  y represents a carbon atom or a sulfur atom;
  n represents 0 or 1;
when y represents a sulfur atom then n=0 and $R^3$ does not exist;
  $R^1$ represents H, (C1-C6)alkyl or halogen;
  when $X_1$ represents a nitrogen atom then $R^2$ does not exist;
  when $X_1$ represents a carbon atom then $R^2$ represents H, COOH, (C1-C6)alkyl, (C1-C6)haloalkyl, nitrile, aryl, heteroaryl, arylcarbonyl, CONR11R12, NR13R14, O—(C1-C6)alkyl or SO$_2$NR15R16, COR17; with
    R11 represents H or (C1-C6)alkyl;
    R12 represents H, (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl or aryl-(C1-C6)alkyl;
    R13 represents H or CH$_3$;

R14 represents H, $CH_3$, (C1-C6)alkyl, (C1-C6)alkylcarbonyl, aryloxycarbonyl, or heteroarylcarbonyl;
R15 represents $CH_3$;
R16 represents $CH_3$;
R17 represents (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl, (C1-C6)alkoxyalkyl or aryl-(C1-C6)alkyl;
$R^3$ represents H, (C1-C6)alkyl or halogen;
$R^4$ represents H, Cl, CN, $NO_2$, NHR18 or OR19 with
R18 represents H, (C1-C6)alkyl, aryl, heteroaryl or (C1-C6)alkylcarbonyl;
R19 represents H or (C1-C6)alkyl;
when $X_2$ represents a nitrogen atom then $R^5$ does not exist;
when $X_2$ represents a carbon atom then $R^5$ represents aryl, heteroaryl, heterocycle, aminoheteroaryl, aminoaryl, (C1-C6)alkylheteroaryl, (C1-C6)alkylcarbonyl, aryloxycarbonyl, heteroarylcarbonyl, oxy(C1-C6)alkylcarbonyl, oxyaryl, OR20 or NR21R22 with
R20 represents H, (C1-C6)alkyl, aryl, heterocycle, (C1-C6)alkylcarbonylheterocycle or heteroaryl;
R21 represents H or (C1-C6)alkyl;
R22 represents H, (C1-C6)alkyl, aryl, heteroaryl, (C1-C6)alkyl-N((C1-C6)alkyl)$_2$, (C1-C6)alkyl-NH(C1-C6)alkyl, (C1-C6)alkyl-$NH_2$, (C1-C6)alkylheteroaryl, heteroarylcarbonyl, COR23, (C1-C6)alkylcarbonyl, aryloxycarbonyl or heteroarylcarbonyl;
R21 and R22 represents together a (C3-C10)cycloalkyl or a oxy(C3-C10)cycloalkyl;
R23 represents (C1-C6)alkyl, aryl, heteroaryl, (C1-C6)alkylheteroaryl, (C1-C6)alkoxyaryl or (C1-C6)alkyloxyaryl;
when $X_3$ represents a carbon atom then $R^6$ represents H, OH, $CH_3$, (C1-C6)alkoxy or (C1-C6)alkyl;
when $X_3$ represents a nitrogen atom and $X_2$ represents a carbon atom and the cycle including $X_2$, $X_3$ and $R^9$ is saturated with no double bond, then $R^6$ represents a (C1-C6)alkanoic acid amide where the nitrogen atom is substituted by R24 and R25, with R24 and R25 represents independently H, (C1-C6)alkyl, aryl, heteroaryl or heterocycle;
$R^7$ represents H, N or $CH_3$.

Any one of the below described embodiments can be combined together, and combined with the compound of formula (II) described above.

According to one particular embodiment of the compounds of formula (II) of the invention, the formula (II) is the formula (IIa) below:

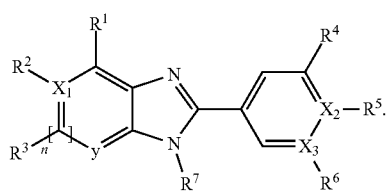

(IIa)

According to one particular embodiment of the compounds of formula (II) of the invention, the formula (II) is the formula (IIb) below:

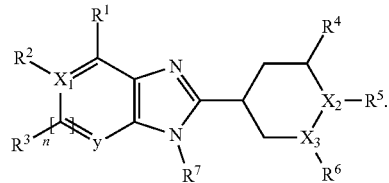

(IIb)

According to one particular embodiment of the compounds of formula (II) of the invention, $R^1$ is H or $CH_3$, the remaining other chemical groups of the compound of formula (II) are as defined above, including their variants.

According to one particular embodiment of the compounds of formula (II) of the invention, $X_1$ is a carbon atom, the remaining other chemical groups of the compound of formula (II) are as defined above, including their variants.

According to one particular embodiment of the compounds of formula (II) of the invention, $R^2$ is CONR11R12 with
R11 representing H or (C1-C6)alkyl;
R12 representing H, (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl or aryl-(C1-C6)alkyl; and
the remaining other chemical groups of the compound of formula (II) being as defined above, including their variants.

According to one particular embodiment of the compounds of formula (I) of the invention, $R^2$ is CONR11R12 with R11 represents H or $CH_3$, and R12 represents a (C1-C6)alkoxyheteroaryl, (C1-C6)alkylheteroaryl or heteroaryl, the remaining other chemical groups of the compound of formula (II) are as defined above, including their variants.

According to one particular embodiment of the compounds of formula (II) of the invention, $R^2$ is CONR11R12 with R11 represents H or $CH_3$, and R12 represents a pyridil, an alkoxylpyridil group or an ethylpyridyl, the remaining other chemical groups of the compound of formula (II) are as defined above, including their variants.

According to one particular embodiment of the compounds of formula (II) of the invention, $R^3$ is H or $CH_3$, the remaining other chemical groups, of the compound of formula (II) are as defined above including their variants.

According to one particular embodiment of the compounds of formula (II) of the invention, y represents a carbon atom and n is equal to 1, the remaining other chemical groups of the compound of formula (II) are as defined above, including their variants. According to one particular embodiment of the compounds of formula (II) of the invention, $R^7$ represents H or $CH_3$, the remaining other chemical groups of the compound of formula (II) are as defined above, including their variants.

According to one particular embodiment of the compounds of formula (II) of the invention, $X_3$ is a carbon atom, the remaining other chemical groups of the compound of formula (II) are as defined above, including their variants.

According to one particular embodiment of the compounds of formula (II) of the invention, $X_2$ is a carbon atom, the remaining other chemical groups of the compound of formula (II), are as defined above including their variants.

According to one particular embodiment of the compounds of formula (II) of the invention, $R^5$ represents NR21R22 with R21 representing H or (C1-C6)alkyl;

R22 representing H, (C1-C6)alkyl, aryl, heteroaryl, (C1-C6)alkyl-N((C1-C6)alkyl)$_2$, (C1-C6)alkyl-NH(C1-C6)alkyl, heteroarylcarbonyl, COR23, (C1-C6)alkylcarbonyl, aryloxycarbonyl or heteroarylcarbonyl; and the remaining other chemical groups of the compound of formula (II) being as defined above, including their variants.

According to one particular embodiment of the compounds of formula (II) of the invention, $R^5$ represents NR21R22 with R21 and R22 each represent, independently of one another, H, or (C1-C6)alkyl, such as H or CH$_3$, the remaining other chemical groups of the compound of formula (II) are as defined above, including their variants. According to one particular embodiment of the compounds of formula (II) of the invention, $R^6$ represents H, or (C1-C6)alkyl, such as H or CH$_3$, the remaining other chemical groups of the compound of formula (II) are as defined above, including their variants. According to one particular embodiment of the compounds of formula (II) of the invention, $R^4$ represents H, or (C1-C6)alkyl, such as H or CH$_3$, the remaining other chemical groups of the compound of formula (II) are as defined above, including their variants.

Any one of the above described embodiments can be combined together with any one of another embodiment of the list. Any one of the variants cited below can be combined together, and with the compound of formula (II) described above.

Advantageously, for the compounds of formula (II), $R^7$ represents H, $X^2$ and $X^3$ are carbon atoms, $R^6$ is H and $R^5$ represents NR21R22 with R21 representing H or (C1-C6)alkyl;

R22 representing H, (C1-C6)alkyl, aryl, heteroaryl, (C1-C6)alkyl-N((C1-C6)alkyl)$_2$, (C1-C6)alkyl-NH(C1-C6)alkyl, heteroarylcarbonyl, COR23, (C1-C6)alkylcarbonyl, aryloxycarbonyl or heteroarylcarbonyl; and the remaining other chemical groups of the compound of formula (II) being as defined above, including their variants.

Advantageously, for the compounds of formula (II), $R^7$ represents H, $R^{10}$ and $R^8$ does not exist, $X_2$ and $X_3$ are carbon atoms, $R^6$ is H and $R^5$ represents NR21R22 with R21 representing H, or (C1-C6)alkyl, such as H or CH$_3$;

R22 representing H, or (C1-C6)alkyl, such as H or CH$_3$; and the remaining other chemical groups of the compound of formula (II) being as defined above, including their variants.

Advantageously, the compounds of formula (II) may notably be chosen from among compounds 1 to 46, such as compounds 1 to 3, 5 to 10, 12 to 16, 19, 24 to 26, 28 to 35, 37, 38, 40 to 42, 45 and 46, preferably compounds 2, 6, and 7, as disclosed in the examples and the pharmaceutically acceptable salts thereof.

The invention relates also to a compound of formula (III) below

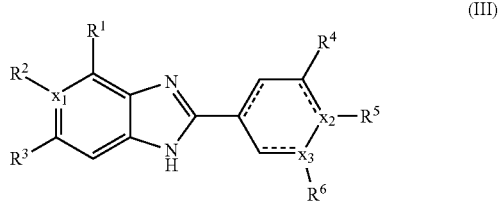

(III)

wherein
$X_1$, $X_2$ and $X_3$ represent a carbon atom;
$R^1$ represents H;
$R^2$ represents H, CH$_3$, CF$_3$, CN, COOH, (C1-C6)alkyl, (C1-C6)alkylcarbonyl, aryloxycarbonyl, heteroarylcarbonyl, nitrile, aryl, heteroaryl, arylcarbonyl, CONR26R27 or NR28R29; with
R26 representing H or CH$_3$;
R27 representing H, (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl or aryl-(C1-C6)alkyl;
R28 representing H or CH$_3$;
R29 representing H, CH$_3$, (C1-C6)alkyl, (C1-C6)alkylcarbonyl, aryloxycarbonyl or heteroarylcarbonyl;
$R^3$ represents H;
$R^4$ represents H;
$R^5$ represents NR30R31 with R30 and R31 represent H or (C1-C6)alkyl;
$R^6$ represents H or CH$_3$.

Any one of the below described embodiments can be combined together, and combined with the compound of formula (III) described above.

According to one particular embodiment of the compounds of formula (III) of the invention, the formula (III) is the formula (IIIa) below:

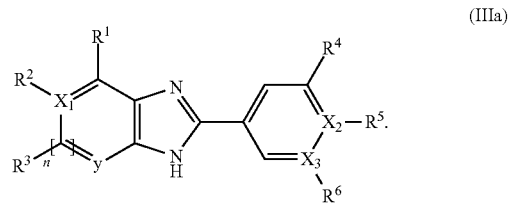

(IIIa)

According to one particular embodiment of the compounds of formula (III) of the invention, the formula (III) is the formula (IIIb) below:

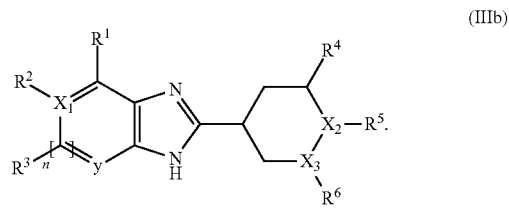

(IIIb)

According to one particular embodiment of the compounds of formula (III) of the invention, $R^2$ represents CONR26R27 with R26 representing H or CH$_3$;

R27 representing H, (C1-C6)alkyl, aryl, heteroaryl, (C1-C6)alkoxyheteroaryl, (C1-C6)alkoxyaryl, haloaryl, (C1-C6)alkoxyalkyl, (C1-C6)alkylheteroaryl, aminoaryl or aryl-(C1-C6)alkyl; and the remaining other chemical groups of the compound of formula (III) being as defined above, including their variants.

According to one particular embodiment of the compounds of formula (III) of the invention, R$^2$ represents CONR26R27 with Benzoimidazoles of Formula I as defined on scheme 1 may be prepared in a multi-step sequence from 3,4-diamino-benzoic acid ethyl ester i and an appropriately substituted aldehyde iia with a reagent such as NaHSO$_3$ or Na$_2$S$_2$O$_5$ and for some compounds without reagents. Alternatively, the benzoimidazoles of Formula iii may be prepared from 3,4-diamino-benzoic acid ethyl ester i and an appropriately substituted carboxylic acid iib with a reagent such as polyphosphoric acid. Saponification of iii and amidation of the resulting carboxylic acid iv with an appropriately substituted amine v with a coupling reagent such as EDCI or HATU produces benzoimidazoles of Formula I.

Scheme 1

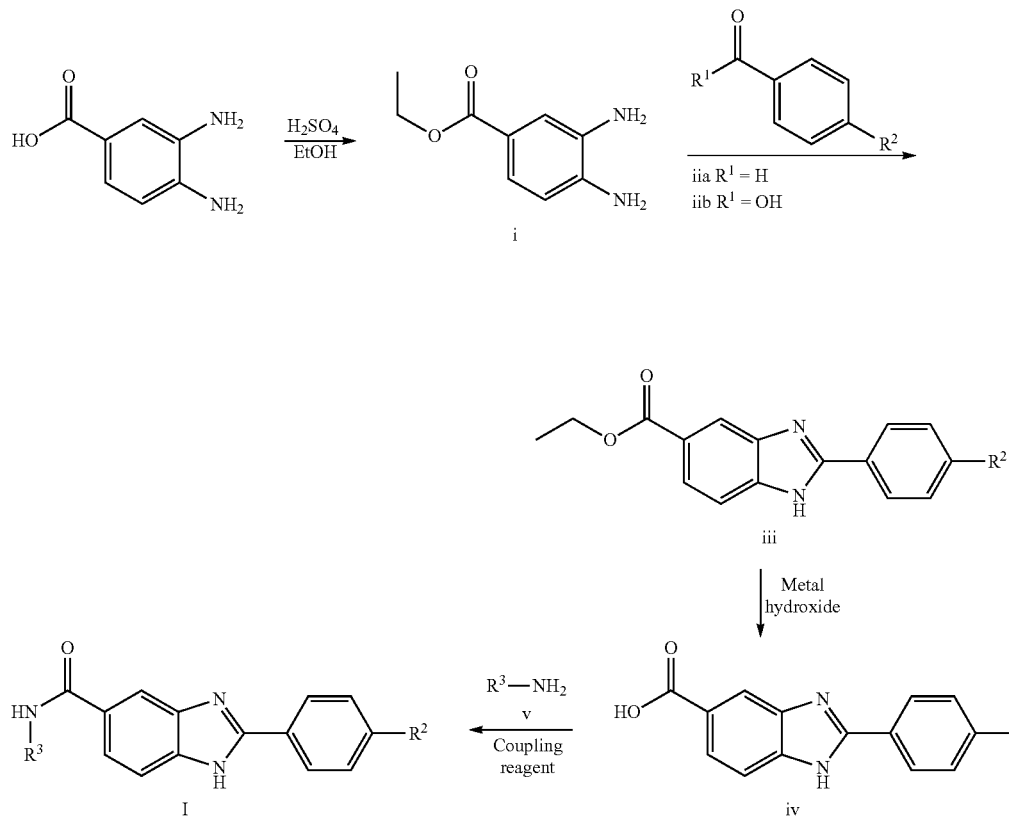

R26 representing H;

R27 representing heteroaryl, (C1-C6)alkoxyheteroaryl, (C1-C6)alkoxyaryl; and the remaining other chemical groups of the compound of formula (III) being as defined above, including their variants.

Any one of the above described embodiments can be combined together with any one of another embodiment of the list. The invention relates also to a compound of formula (I') as defined above according to any one of its embodiments disclosed above. Preferably, compounds of formula (I), (I') (II) or (III) may notably be chosen from among compounds 1 to 44, such as compounds 1 to 3, 5 to 10, 12 to 16, 19, 24 to 26, 28 to 35, 37, 38, and 40 to 42, preferably compounds 2, 6, and 7, as disclosed in the examples and the pharmaceutically acceptable salts thereof.

The compounds of the present invention can be prepared according to the synthetic routes outlined in Schemes 1, 2 and 3 below and by the following methods described therein.

Benzoimidazoles of Formula II as defined on scheme 2 may be prepared in a multi-step sequence from 2-(4-nitro-phenyl)-3H-benzoimidazole-5-carboxylic acid ethyl ester iiib. The reduction of the nitro group provides the corresponding 2-(4-amino-phenyl)-3H-benzoimidazole-5-carboxylic acid ethyl ester vi which may be substituted with the appropriately substituted carboxylic acid vii. Then the amide viii may be hydrolyzed to the carboxylic acid ix and may reacts with the appropriately substituted amine v and a coupling reagent to produce benzoimidazoles of Formula II. Alternatively, the 2-(4-nitro-phenyl)-3H-benzoimidazole-5-carboxylic acid ethyl ester iiib may be hydrolyzed to the corresponding 2-(4-nitro-phenyl)-3H-benzoimidazole-5-carboxylic acid ivb which can react with the appropriately substituted amine v to give the amide x. Reduction of the nitro derivative x and coupling of the resulting amine with the appropriately substituted carboxylic acid vii and a coupling reagent produces benzoimidazoles of Formula II.

Scheme 2

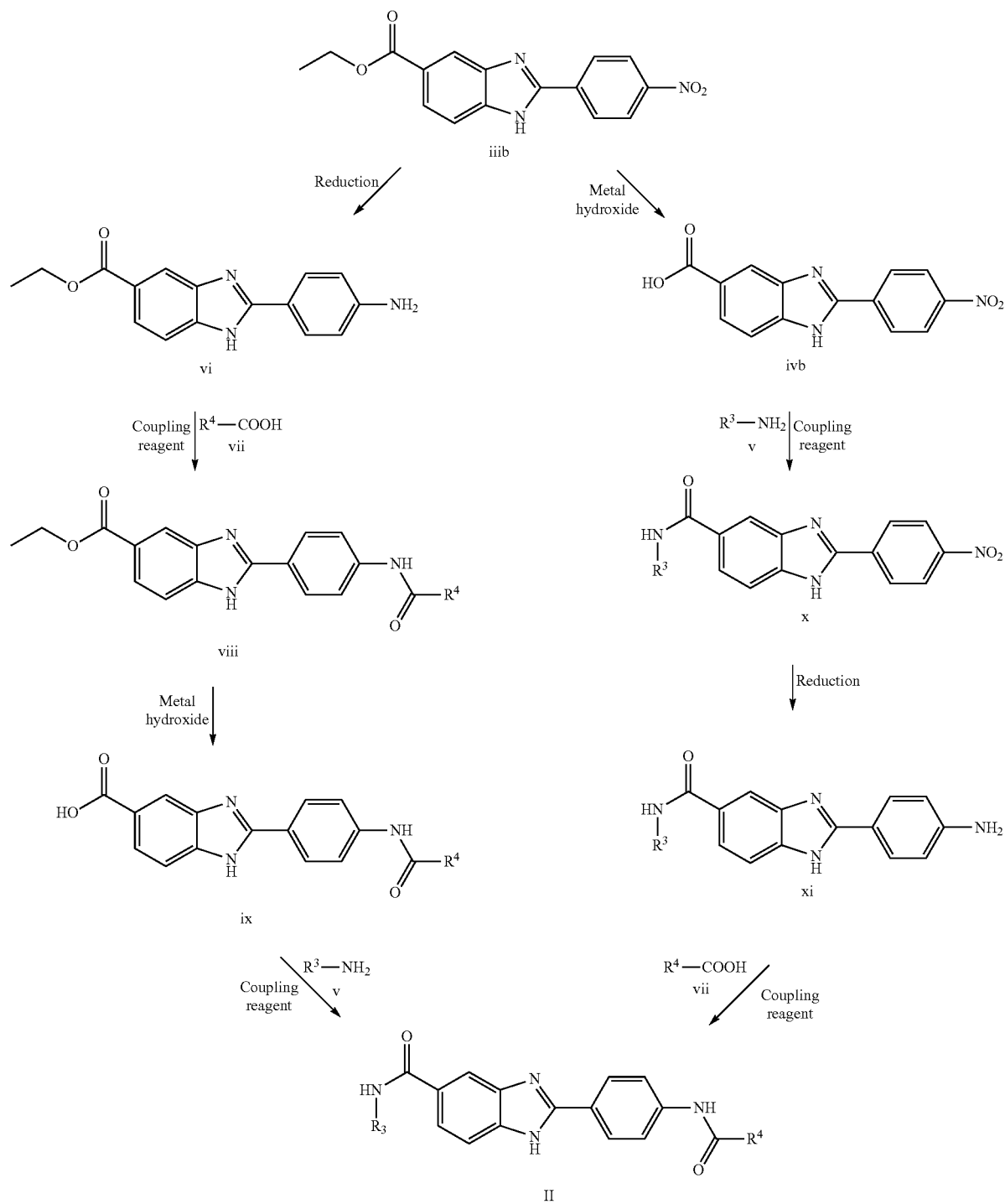

Benzoimidazoles of Formula III as defined on scheme 3 may be prepared in a multi-step sequence from 3,4-diamino-benzamide xiia, or from (3,4-diamino-phenyl)-phenyl-methanone xiib, or from 3,4-diamino-benzonitrile xiic, or from 3,5-dimethylbenzene-1,2-diamine xiid, or from 5-chloro-3-methylbenzene-1,2-diamine xiie, or from 4-Pyrimidin-2-yl-benzene-1,2-diamine xiif, or from 4-nitro-benzene-1,2-diamine xiig, or from 4-(trifluoromethyl)benzene-1,2-diamine xiih, and an appropriately substituted aldehyde iia with a reagent such as NaHSO$_3$ or Na$_2$S$_2$O$_5$. Alternatively, benzoimidazoles of Formula III may be prepared from 3,4-diamino-benzamide xiia, or from (3,4-diamino-phenyl)-phenyl-methanone xiib, or from 3,4-diamino-benzonitrile xiic, or from 3,5-dimethyl-benzene-1,2-diamine xiid, or from 5-chloro-3-methyl-benzene-1,2-diamine xiie, or from 4-Pyrimidin-2-yl-benzene-1,2-diamine xiif, or from 4-nitro-benzene-1,2-diamine xiig, or from 4-(trifluoromethyl)benzene-1,2-diamine xiih, and an appropriately substituted carboxylic acid iib with a reagent such as polyphosphoric acid.

Scheme 3

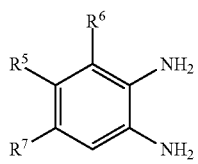 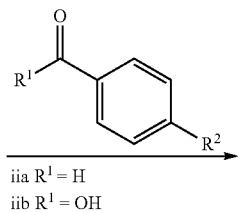

iia R¹ = H
iib R¹ = OH xiia R⁵ = CONH₂, R⁶ = H, R⁷ = H
xxiib R⁵ = COPh, R⁶ = H, R⁷ = H
xiic R⁵ = CN, R6 = H, R7 = H
xiid R⁵ = H, R⁶ = CH₃, R⁷ = CH₃
xiie R⁵ = H, R⁶ = CH₃, R⁷ = Cl
xiif R⁵ = pyridin-2-yl, R⁶ = H, R⁷ = H
xiig R⁵ = NO₂, R⁶ = H, R⁷ = H
xiih R⁵ = CF₃, R⁶ = H, R⁷ = H

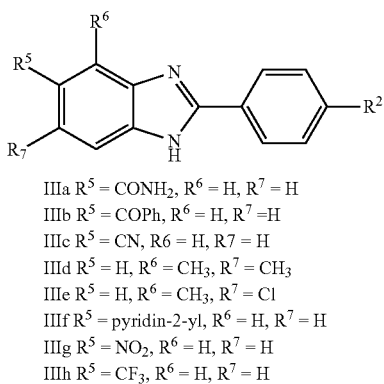

IIIa R⁵ = CONH₂, R⁶ = H, R⁷ = H
IIIb R⁵ = COPh, R⁶ = H, R⁷ = H
IIIc R⁵ = CN, R6 = H, R7 = H
IIId R⁵ = H, R⁶ = CH₃, R⁷ = CH₃
IIIe R⁵ = H, R⁶ = CH₃, R⁷ = Cl
IIIf R⁵ = pyridin-2-yl, R⁶ = H, R⁷ = H
IIIg R⁵ = NO₂, R⁶ = H, R⁷ = H
IIIh R⁵ = CF₃, R⁶ = H, R⁷ = H

EXAMPLES

The following abbreviations have been used in the examples:
DCM: Dichloromethane
DIPEA: Diisopropylethylamine
DMAP: Dimethylaminopyridine
DMF: Dimethylformamid
DMSO: Dimethylsulfoxide
EDCI: 1-Ethyl-3-(3-dimethylaminopropyl)carbodiimide
HATU: 1-[Bis(dimethylamino)methylene]-1H-1,2,3-triazolo[4,5-b]pyridinium 3-oxid hexafluorophosphate
MS: Mass Spectrum
NMR: Nuclear Magnetic Resonance
PyBOP: (1H-Benzotriazol-1-yloxy)tripyrrolidinophosphonium hexafluorophosphate
THF: Tetrahydrofurane
TLC: Thin Layer Chromatography
1/Chemistry—Methods of Synthesis Example 1

2-(4-dimethylamino-phenyl)-1H-benzoimidazole-5-carboxylic Acid (3-methoxy-phenyl)-amide

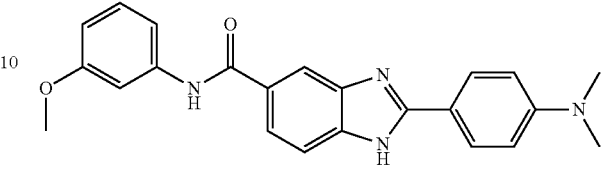

Step 1 Preparation of 3,4-diamino-benzoic acid ethyl ester i

To a stirred solution of 3,4-diamino-benzoic acid (500 mg, 3.29 mmol) in ethanol (20 mL) conc. H₂SO₄ (2 mL) was added drop wise at 0 to 5° C. and the resulting solution was heated to reflux at 85° C. for 18 hours. Reaction was monitored by TLC. After completion of reaction ethanol was evaporated, the residue obtained was basified with saturated bicarbonate solution, extracted with ethyl acetate, dried over Na₂SO₄ and concentrated under reduced pressure to obtain 3,4-diamino-benzoic acid ethyl ester i (500 mg, 84% yield). MS m/z (M+H) 181.3.

Step 2: Preparation of 2-(4-dimethylamino-phenyl)-1H-benzoimidazole-5-carboxylic acid ethyl ester To a stirred solution of 3,4-diamino-benzoic acid ethyl ester i (0.36 g, 0.002 moles, 1 eq) and 4-dimethylamino-benzaldehyde (0.45 g, 0.003 moles) in DMF (5 mL), sodium bisulfite (360 mg, 0.03 mmol) was added and the resulting reaction mixture was heated at 150° C. for 3 hrs. Reaction was monitored by TLC. After completion of reaction the reaction mixture was added to crushed ice to get crude product as a pale yellow solid which was further purified by recrystallization from hot methanol to obtain 2-(4-dimethylamino-phenyl)-1H-benzoimidazole-5-carboxylic acid ethyl ester as an off white solid (247 mg, 41% yield). MS m/z (M+H) 310.0.

Step 3: 2-(4-Dimethylamino-phenyl)-1H-benzoimidazole-5-carboxylic acid

To a solution of 2-(4-dimethylamino-phenyl)-1H-benzoimidazole-5-carboxylic acid ethyl ester (0.43 g, 0.0014 moles) in methanol (10 mL) at 25° C., NaOH (0.569 g, 0.014 moles) in water (5 mL) was added and the resulting reaction mixture was stirred at 60° C. for 12 hrs. Reaction was monitored by TLC. After the completion of reaction, the resulting reaction mixture was evaporated under reduced pressure. The residue obtained was dissolved in minimum water and was acidified slowly to pH 3 using 1.5 N HCl to get crude product as pale a yellow solid which was further purified with normal phase column chromatography using 230-400 silica gel in methanol/DCM solvent system (product eluted at 5% methanol in DCM) to get 2-(4-Dimethylamino-phenyl)-1H-benzoimidazole-5-carboxylic acid as an off white solid (300 mg, 76% yield). MS m/z (M+H) 281.9.

Step 4: 2-(4-dimethylamino-phenyl)-1H-benzoimidazole-5-carboxylic acid (3-methoxy-phenyl)-amide To a solution of 2-(4-Dimethylamino-phenyl)-1H-benzoimidazole-5-carboxylic acid (195 mg, 0.694 mmol, 1 eq) in DMF (10 mL) at 25° C., EDCI (200 mg, 1.04 mmol, 1.5 eq), 3-methoxy-phenylamine (128 mg, 1.04 mmol, 1.5 eq) and DMAP (17 mg, 0.138 mmol, 0.2 eq) were added. The resulting reaction mass was warmed to 25° C. and was stirred for 16 hrs and the reaction was monitored by TLC.

After completion of reaction the reaction mixture from above was added to crushed ice and filtered. The solid obtained was purified by column chromatography using silica gel 230-400 in DCM/methanol solvent system. The product obtained was further purified by recrystallization from methanol to obtain 2-(4-dimethylamino-phenyl)-1H-benzoimidazole-5-carboxylic acid (3-methoxy-phenyl)-amide as an off-white solid (92 mg, 36% yield). $^1$H NMR (400 MHz, DMSO-$d_6$) δ 12.82 (d, J=5.3 Hz, 1H), 10.17 (d, J=24.6 Hz, 1H), 8.27 (s, 1H), 8.08-7.98 (m, 3H), 7.78 (ddd, J=8.7, 3.9, 1.7 Hz, 1H), 7.53 (dd, J=7.9, 2.8 Hz, 1H), 7.41 (dd, J=10.4, 8.1 Hz, 1H), 7.25 (td, J=8.2, 1.7 Hz, 1H), 6.86 (d, J=8.5 Hz, 2H), 6.67 (dt, J=8.2, 2.5 Hz, 1H), 3.76 (s, 3H), 3.01 (d, J=1.8 Hz, 6H). MS m/z (M+H) 387.0.

Example 2

2-(4-Dimethylamino-phenyl)-1H-benzoimidazole-5-carboxylic Acid pyridin-4-ylamide

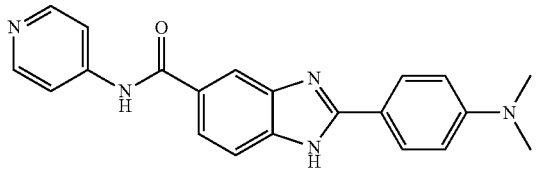

2-(4-Dimethylamino-phenyl)-1H-benzoimidazole-5-carboxylic acid pyridin-4-ylamide was synthesized from 2-(4-dimethylamino-phenyl)-1H-benzoimidazole-5-carboxylic acid and pyridin-4-ylamine by following the procedure for example 1. $^1$H NMR (400 MHz, DMSO-d6) δ 12.87 (s, 1H), 10.60 (d, J=36.9 Hz, 1H), 8.47 (d, J=5.4 Hz, 2H), 8.26 (s, 1H), 8.04 (m, 3H), 7.82 (dd, J=12.0, 7.1 Hz, 2H), 7.67-7.47 (m, 1H), 6.86 (d, J=8.5 Hz, 2H), 3.02 (s, 6H). MS m/z (M+H) 358.0.

Example 3

2-(4-Dimethylamino-phenyl)-1H-benzoimidazole-5-carboxylic Acid (2-methoxy-ethyl)-amide

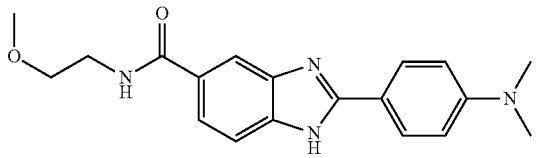 [SMILES: COCCNC(=O)c1ccc2[nH]c(-c3ccc(N(C)C)cc3)nc2c1]

2-(4-Dimethylamino-phenyl)-1H-benzoimidazole-5-carboxylic acid (2-methoxy-ethyl)-amide was synthesized from 2-(4-dimethylamino-phenyl)-1H-benzoimidazole-5-carboxylic acid and 2-methoxy-ethylamine by following the procedure for example 1. $^1$H NMR (400 MHz, DMSO-d6) δ 12.73 (s, 1H), 8.45 (d, J=15.6 Hz, 1H), 8.13-7.91 (m, 3H), 7.67 (d, J=8.6 Hz, 1H), 7.51 (dd, J=43.5, 8.5 Hz, 1H), 6.84 (d, J=8.7 Hz, 2H), 3.46 (qd, J=8.8, 8.3, 3.3 Hz, 4H), 3.28 (s, 3H), 3.01 (s, 6H). MS m/z (M+H) 339.1.

Example 4

2-(4-Dimethylamino-phenyl)-3H-benzoimidazole-5-carboxylic Acid Amide

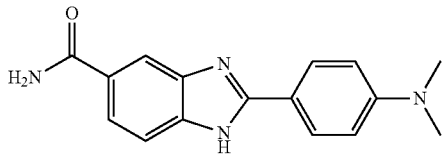 [SMILES: CN(C)c1ccc(-c2nc3cc(C(N)=O)ccc3[nH]2)cc1]

2-(4-Dimethylamino-phenyl)-3H-benzoimidazole-5-carboxylic acid amide was prepared using 3,4-diaminobenzamide and 4-dimethylamino-benzaldehyde by following the procedure for example 1. $^1$H NMR (400 MHz, DMSO-d6) δ 12.79 (s, 1H), 8.02-7.93 (m, 4H), 7.71 (dd, J=8.8, 1.2 Hz, 1H), 7.50 (d, J=7.2 Hz, 1H), 7.22 (s, 1H), 6.84 (d, J=9.2 Hz, 2H), 3.01 (s, 6H). MS m/z (M+H) 281.0.

Example 5

2-(4-Dimethylamino-phenyl)-3H-benzoimidazole-5-carboxylic Acid Dimethyl Amide

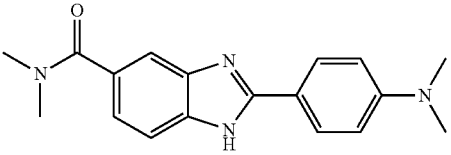

2-(4-Dimethylamino-phenyl)-3H-benzoimidazole-5-carboxylic acid dimethyl amide was prepared using 2-(4-dimethylamino-phenyl)-1H-benzoimidazole-5-carboxylic acid and dimethyl amine (2M) in THF by following the procedure for example 1. $^1$H NMR (400 MHz, DMSO-d6) δ 12.71 (s, 1H), 8.03-7.93 (m, 2H), 7.57 (d, J=9.9 Hz, 1H), 7.46 (d, J=7.4 Hz, 1H), 6.84 (d, J=8.9 Hz, 2H), 3.29 (s, 1H), 3.00 (d, J=5.1 Hz, 12H). MS m/z (M+H) 309.1.

Example 6

2-(4-Dimethylamino-phenyl)-1H-benzoimidazole-5-carboxylic Acid (6-methoxy-pyridin-3-yl)-amide

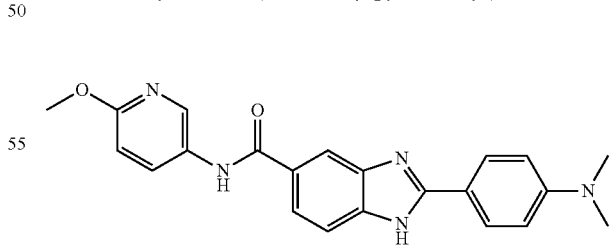

Step 1: 2-(4-dimethylamino-phenyl)-1H-benzoimidazole-5-carboxylic acid ethyl ester
1.00 g (6.7 mmol, 1.00 eq) of 4-(dimethylamino)-benzaldehyde was dissolved in ethanol and sodium metabisulfite 1.9 g (10 mmol, 1.50 eq) in water was added in 3 portions. After addition of reagent the reaction mixture was vigorously shaked for 1 minute and additionally for 5 minutes after last addition. Then left for 1 h (shaked every 20 minutes) and cooled down with ice bath. The formed precipitate was filtered, washed with 2× cold water and 2×EtOH, and dried in vacuum to afford sodium bisulfite adducts. To the crude (1.19 g, yield 70%) was added 3,4-diamino-benzoic acid ethyl ester i, which was prepared following the procedure described in example 1, and both were dissolved in DMF (23 ml). The reaction mixture was stirred at 90° C. under Ar atmosphere for 19 h. The reaction mixture was diluted in ethyl acetate (75 mL) and washed with water (3×25 mL). The water layers were combined, washed 3×10 ml of AcOEt. Combined organic layers were dried over $Na_2SO_4$, filtrated and evaporated under reduced pressure to afford crude products. 2-(4-dimethylamino-phenyl)-1H-benzoimidazole-5-carboxylic acid ethyl ester was obtained after recrystallization from ethanol/$CH_2Cl_2$ as an off-white solid (0.9 g, 69% yield). MS m/z (M+H) 310.3.

Step 2: 2-(4-Dimethylamino-phenyl)-1H-benzoimidazole-5-carboxylic acid

To a stirred solution of 2-(4-dimethylamino-phenyl)-1H-benzoimidazole-5-carboxylic acid ethyl ester (2.445 g, 7.9 mmol, 1.00 eq) in THF (25 ml) was added a solution of $LiOH.H_2O$ (1 g, 24.5 mmol, 3.12 eq) in $H_2O$ (12 ml). The reaction mixture was stirred at room temperature overnight and at 80° C. during 7 h. Additional $LiOH.H_2O$ (1 g, 24.5 mmol, 3.12 eq) in $H_2O$ (12 ml) was added and heating was continued overnight. The reaction mixture was diluted with 150 ml of water and acidified by 6N HCl up to pH=6. The resulting precipitate was collected by filtration, washed with water (3×10 ml) and dried in vacuum to afford the 2-(4-Dimethylamino-phenyl)-1H-benzoimidazole-5-carboxylic acid (2.2 g, 99% yield). MS m/z (M+H) 282.1.

Step 3: 2-(4-Dimethylamino-phenyl)-1H-benzoimidazole-5-carboxylic acid (6-methoxy-pyridin-3-yl)-amide 2-(4-Dimethylamino-phenyl)-1H-benzoimidazole-5-carboxylic acid (1.2 g, 4.25 mol, 1.00 eq) was dissolved in dry DMF (12.5 ml) then HATU (1.78 g, 4.7 mmol, 1.2 eq) and DIPEA (2.2 ml, 12.8 mmol, 3 eq) were added at 0° C. After 30 minutes to this mixture a solution of 6-methoxypyridin-3-amine (1.06 g, 8.5 mmol, 2.00 eq) in dry DCM (12.5 ml) was added. The reaction mixture was stirred 3 days under Ar atmosphere. Then water (20-100 ml) and AcOEt (5-75 ml) were added, the mixture was transferred to a flask with stopper. After vigorous shaking the precipitate appears. The solid was filtered and washed with minimal amount of water (1×) and AcOEt (2×). The solid was dried in vacuum for 24 h to afford 2-(4-Dimethylamino-phenyl)-1H-benzoimidazole-5-carboxylic acid (6-methoxy-pyridin-3-yl)-amide as an off-white solid (1.237 g, 75% yield). $^1$H NMR (400 MHz, DMSO-d6) δ 12.93 (s, 1H), 10.25 (s, 1H), 8.55 (d, J=2.7 Hz, 1H), 8.17 (s, 1H), 8.13-7.99 (m, 3H), 7.81 (dd, J=8.3, 1.7 Hz, 1H), 7.60 (d, J=8.3 Hz, 1H), 6.86 (dd, J=8.9, 4.0 Hz, 3H), 3.85 (s, 3H), 3.02 (s, 6H). MS m/z (M+H) 387.8.

Example 7

2-(4-Dimethylamino-phenyl)-1H-benzoimidazole-5-carboxylic Acid (6-ethylpyridin-3-yl)-amide

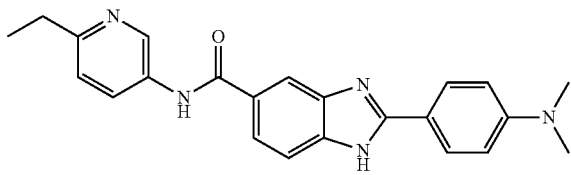 [SMILES: CCc1ccc(NC(=O)c2ccc3[nH]c(-c4ccc(N(C)C)cc4)nc3c2)cn1]

2-(4-Dimethylamino-phenyl)-1H-benzoimidazole-5-carboxylic acid (6-methoxy-pyridin-3-yl)-amide was prepared using 2-(4-dimethylamino-phenyl)-1H-benzoimidazole-5-carboxylic acid and 6-ethylpyridin-3-amine in DMF/$CH_2Cl_2$ 1:1 by following the procedure for example 6. $^1$H NMR (400 MHz, DMSO-d6) δ 12.83 (s, 1H), 10.31 (m, 1H), 8.85 (d, J=4 Hz, 1H), 8.13 (m, 1H), 8.04 (dd, J=8 Hz, 2H), 7.81 (d, J=8 Hz, 1H), 7.60 (m, 1H), 7.26 (d, J=8 Hz, 1H), 6.86 (d, J=8 Hz, 2H), 3.02 (s, 6H), 2.73 (q, J=8 Hz, 2H), 1.23 (t, J=8 Hz, 3H). MS m/z (M+H) 386.3.

Example 8

2-(4-Dimethylamino-phenyl)-1H-benzoimidazole-5-carboxylic Acid (6-isopropylpyridin-3-yl)-amide

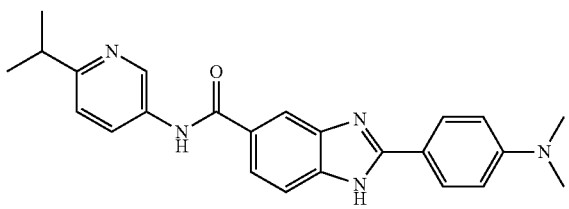 [SMILES: CC(C)c1ccc(NC(=O)c2ccc3[nH]c(-c4ccc(N(C)C)cc4)nc3c2)cn1]

2-(4-Dimethylamino-phenyl)-1H-benzoimidazole-5-carboxylic acid (6-isopropylpyridin-3-yl)-amide was prepared using 2-(4-dimethylamino-phenyl)-1H-benzoimidazole-5-carboxylic acid and 6-isopropylpyridin-3-amine in DMF/$CH_2Cl_2$ 1:1 by following the procedure for example 6. $^1$H NMR (400 MHz, DMSO-d6) δ 12.82 (d, J=4 Hz, 1H), 10.32 (d, J=24 Hz, 1H), 8.85 (dd, J=4 Hz, 1H), 8.29 (s, 1H), 8.13 (ddd, J=4 Hz, 1H), 8.04 (dt, J=4 Hz, 2H), 7.66 (d, J=8 Hz, 1H), 7.66 (d, J=12 Hz, 0.5H), 7.54 (d, J=12 Hz, 0.5H), 7.27 (d, J=8 Hz, 1H), 6.86 (d, J=8 Hz, 2H), 3.01 (m, 7H), 1.24 (d, J=8 Hz, 6H). MS m/z (M+H) 400.3.

Example 9

2-(4-Dimethylamino-phenyl)-1H-benzoimidazole-5-carboxylic Acid (4-dimethylamino-phenyl)-amide

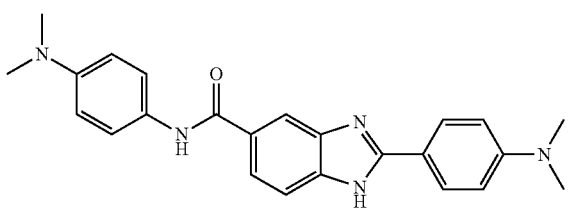

2-(4-Dimethylamino-phenyl)-1H-benzoimidazole-5-carboxylic acid (4-dimethylamino-phenyl)-amide was prepared using 2-(4-dimethylamino-phenyl)-1H-benzoimidazole-5-carboxylic acid and N,N-dimethylbenzene-1,4-diamine in DMF/$CH_2Cl_2$ 1:1 by following the procedure for example 6. $^1$H NMR (400 MHz, DMSO-d6) δ 12.77 (s, 1H), 9.93 (d, J=20 Hz, 1H), 8.24 (s, 0.5H), 8.03 (m, 2.5H), 7.78 (d, J=8 Hz, 1H), 7.61 (m, 2.5H), 7.51 (d, J=8 Hz, 0.5H), 6.85 (m, 2H), 6.73 (dd, J=8 Hz, J=4 Hz, 2H), 3.01 (s, 6H), 2.87 (s, 6H). MS m/z (M+H) 400.4.

Example 10

2-Pyridin-4-yl-1H-benzoimidazole-5-carboxylic Acid Dimethylamide

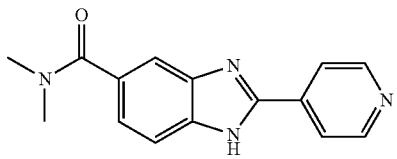 [SMILES: CN(C)C(=O)c1ccc2[nH]c(-c3ccncc3)nc2c1]

Step 1: 2-pyridin-4-yl-3H-benzoimidazole-5-carboxylic acid ethyl ester
2-pyridin-4-yl-3H-benzoimidazole-5-carboxylic acid ethyl ester was prepared using 3,4-diamino-benzoic acid ethyl ester i and pyridine-4-carbaldehyde in DMF following the procedure for example 1. MS m/z (M+H) 268.1.

Step 2: 2-pyridin-4-yl-3H-benzoimidazole-5-carboxylic acid
2-pyridin-4-yl-3H-benzoimidazole-5-carboxylic acid was prepared from 2-pyridin-4-yl-3H-benzoimidazole-5-carboxylic acid ethyl ester by following the procedure for example 1. MS m/z (M+H) 240.5.

Step 3: 2-Pyridin-4-yl-1H-benzoimidazole-5-carboxylic acid dimethylamide
2-pyridin-4-yl-1H-benzoimidazole-5-carboxylic acid dimethylamide was prepared from 2-pyridin-4-yl-3H-benzoimidazole-5-carboxylic acid and N,N-dimethylamine in THF (1M) following the procedure for example 1. $^1$H NMR (400 MHz, DMSO-d6) δ 13.45 (s, 1H), 8.81-8.75 (m, 2H), 8.14-8.07 (m, 2H), 7.69 (d, J=6.9 Hz, 2H), 7.32 (d, J=8.6 Hz, 1H), 3.00 (s, 6H). MS m/z (M+H) 267.0.

Example 11

2-Pyridin-4-yl-1H-benzoimidazole-5-carboxylic Acid benzothiazol-5-ylamide

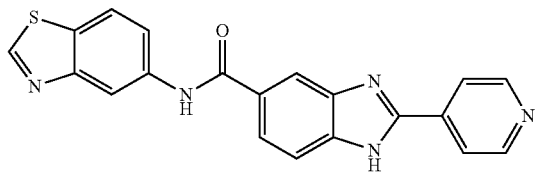 [SMILES: O=C(Nc1ccc2scnc2c1)c1ccc2[nH]c(-c3ccncc3)nc2c1]

Step 1: 2-Pyridin-4-yl-3H-benzoimidazole-5-carboxylic acid
3,4-Diamino-benzoic acid (0.76 g, 5 mmol) was dissolved in 15 mL of N,N-dimethylformamide and one equivalent of pyridine-4-carbaldehyde (0.54 g, 5 mmol) was added. The solution was heated to 80° C. for 5 hours and cooled to room temperature. The precipitate was filtered, washed with methanol and used without further purification (Yield 60%).

Step 2: 2-Pyridin-4-yl-1H-benzoimidazole-5-carboxylic acid benzothiazol-5-ylamide
2-Pyridin-4-yl-3H-benzoimidazole-5-carboxylic acid was solubilized in N,N-dimethylformamide at a 0.1 M concentration with 2 equivalents of diisopropylethylamine. The coupling reagent O-(Benzotriazol-1-yl)-N,N,N',N'-tetramethyluronium tetrafluoroborate (TBTU) was solubilized at 0.1 M in N,N-dimethylformamide. One equivalent was added to the acid solution and the reaction mixture was shaken for 5 minutes. Benzothiazol-6-ylamine was solubilized in N,N-dimethylformamide at a 0.1 M. One equivalent was added to the activated acid solution and the reaction mixture was shaken for 3 hours. The mixture was evaporated and the residue was purified on C18 in a gradient water/methanol with 0.1% ammoniac to afford the final compound as a powder (Yield 75%). MS m/z (M+H) 372.05.

Example 12

2-Pyridin-4-yl-1H-benzoimidazole-5-carboxylic Acid methyl-phenyl-amide

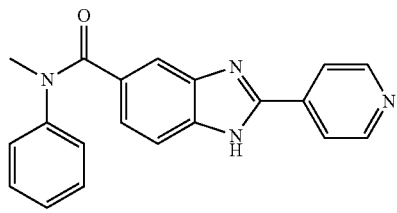 [SMILES: CN(C(=O)c1ccc2[nH]c(-c3ccncc3)nc2c1)c1ccccc1]

2-Pyridin-4-yl-3H-benzoimidazole-5-carboxylic acid methyl-phenyl-amide was prepared using 2-pyridin-4-yl-3H-benzoimidazole-5-carboxylic acid and N-methylaniline by following the procedure for example 1. $^1$H NMR (400 MHz, DMSO-d6) δ 13.34 (d, J=10.5 Hz, 1H), 8.82-8.71 (m, 2H), 8.03 (dd, J=4.7, 1.5 Hz, 2H), 7.60-7.50 (m, 1H), 7.50-7.39 (m, 2H), 7.30-7.14 (m, 5H), 7.13 (d, J=8.1 Hz, 1H), 3.41 (d, J=3.3 Hz, 3H). MS m/z (M+H) 329.1.

Example 13

2-{4-[(1-Methyl-1H-pyrrole-2-carbonyl)-amino]-phenyl}-1H-benzoimidazole-5-carboxylic Acid Phenylamide

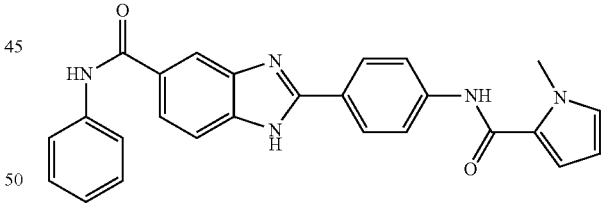

Step 1: 2-(4-nitro-phenyl)-3H-benzoimidazole-5-carboxylic acid ethyl ester iiib
2-(4-nitro-phenyl)-3H-benzoimidazole-5-carboxylic acid methyl ester iiib was prepared using 4-nitro-benzaldehyde and 3,4-diamino-benzoic acid ethyl ester i by following the procedure for example 1. MS m/z (M+H) 312.3.

Step 2: 2-(4-amino-phenyl)-3H-benzoimidazole-5-carboxylic acid ethyl ester vi
To a solution of 2-(4-nitro-phenyl)-3H-benzoimidazole-5-carboxylic acid ethyl ester iiib (500 mg, 1.61 mmol) in methanol (50 mL), Pd/C (10%, 50% wet) (250 mg) was added and was stirred under hydrogen atmosphere (50 psi) for 16 h. The reaction was monitored by TLC. After the completion of reaction, the reaction mass was filtered through Celite® bed and the filtrate concentrated to get the crude product which further purified using flash column chromatography with silica (230-400) and methanol/CH$_2$Cl$_2$ (2-3%) as eluent to obtain pure 2-(4-amino-phenyl)-3H-benzoimidazole-5-carboxylic acid methyl ester vi (270 mg, 59% yield). MS m/z (M+H) 282.4.

Step 3: 2-{4-[(1-Methyl-1H-pyrrole-2-carbonyl)-amino]-phenyl}-1H-benzoimidazole-5-carboxylic acid ethyl ester To a stirred solution of 1-methyl-1H-pyrrole-2-carboxylic acid (100 mg, 0.8 mmoles) in DMF (10 mL) at 25° C., EDCI (230 mg, 1.2 moles), 2-(4-amino-phenyl)-3H-benzoimidazole-5-carboxylic acid ethyl ester vi (320 mg, 1.2 mmoles) and DMAP (20 mg, 0.16 mmol) were added and the resulting reaction mixture was heated at 80° C. for 5 h. The resulting reaction mixture was added to ice cold water and extracted with ethyl acetate. The ethyl acetate layer dried over Na$_2$SO$_4$ and concentrated under reduced pressure to obtain crude product which was purified with normal phase column chromatography using silica gel (230-400) in ethyl acetate/hexane solvent to 2-{4-[(1-Methyl-1H-pyrrole-2-carbonyl)-amino]-phenyl}-1H-benzoimidazole-5-carboxylic acid ethyl ester (120 mg, 38% yield). MS m/z (M+H) 389.6.

Step 4: 2-{4-[(1-Methyl-1H-pyrrole-2-carbonyl)-amino]-phenyl}-1H-benzoimidazole-5-carboxylic acid 2-{4-[(1-Methyl-1H-pyrrole-2-carbonyl)-amino]-phenyl}-1H-benzoimidazole-5-carboxylic acid was prepared from 2-{4-[(1-Methyl-1H-pyrrole-2-carbonyl)-amino]-phenyl}-1H-benzoimidazole-5-carboxylic acid ethyl ester by following the procedure for example 1. MS m/z (M+H) 361.4.

Step 5: 2-{4-[(1-Methyl-1H-pyrrole-2-carbonyl)-amino]-phenyl}-1H-benzoimidazole-5-carboxylic acid phenylamide To a solution of 2-{4-[(1-Methyl-1H-pyrrole-2-carbonyl)-amino]-phenyl}-1H-benzoimidazole-5-carboxylic acid (250 mg, 0.694 mmol, 1 eq) in DMF (10 mL) at 25° C., EDCI (200 mg, 1.04 mmol, 1.5 eq), aniline (100 mg, 1.04 mmol, 1.5 eq) and DMAP (17 mg, 0.138 mmol, 0.2 eq) were added. The resulting reaction mass warmed to 25° C. and was stirred for 16 hrs (Reaction monitored by TLC). After completion, the reaction mixture from above was added to crushed ice, filtered, and the solid obtained purified by column chromatography using silica gel 230-400 in CH$_2$Cl$_2$/methanol solvent system. The product obtained was further purified by recrystallization from methanol to obtain 2-{4-[(1-Methyl-1H-pyrrole-2-carbonyl)-amino]-phenyl}-1H-benzoimidazole-5-carboxylic acid phenylamide as an off white solid (110 mg, 36% yield). $^1$H NMR (400 MHz, DMSO-d6) δ 13.20 (s, 1H), 10.25 (s, 1H), 10.01 (s, 1H), 8.26-8.14 (m, 3H), 7.93 (d, J=8.4 Hz, 2H), 7.83 (d, J=7.7 Hz, 3H), 7.66 (d, J=8.4 Hz, 1H), 7.36 (t, J=7.6 Hz, 2H), 7.08 (dd, J=15.9, 7.7 Hz, 3H), 6.13 (s, 1H), 3.91 (s, 3H). MS m/z (M+H) 436.5.

Example 14

2-{4-[(Oxazole-5-carbonyl)-amino]-phenyl}-1H-benzoimidazole-5-carboxylic Acid Phenylamide

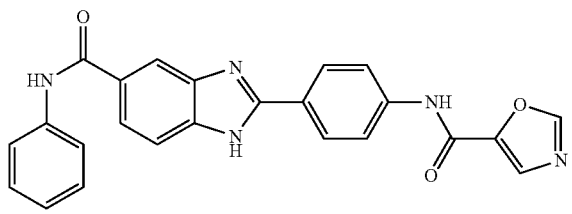 [SMILES: O=C(Nc1ccccc1)c1ccc2[nH]c(-c3ccc(NC(=O)c4cnco4)cc3)nc2c1]

Step 1: 2-(4-nitro-phenyl)-3H-benzoimidazole-5-carboxylic acid ethyl ester iiib 2-(4-nitro-phenyl)-3H-benzoimidazole-5-carboxylic acid methyl ester was prepared using 4-nitro-benzaldehyde and 3,4-diamino-benzoic acid methyl ester by following the procedure for example 1. MS m/z (M+H) 312.3.

Step 2: 2-(4-nitro-phenyl)-3H-benzoimidazole-5-carboxylic acid ivb 2-(4-nitro-phenyl)-3H-benzoimidazole-5-carboxylic acid ivb was prepared from 2-(4-nitro-phenyl)-3H-benzoimidazole-5-carboxylic acid ethyl ester by following the procedure for example 1. MS m/z (M+H) 312.1.

Step 3: 2-(4-nitro-phenyl)-3H-benzoimidazole-5-carboxylic acid phenylamide 2-(4-nitro-phenyl)-3H-benzoimidazole-5-carboxylic acid phenylamide was prepared using 2-(4-nitro-phenyl)-3H-benzoimidazole-5-carboxylic acid and aniline by following the procedure for example 13. MS m/z (M+H) 359.1.

Step 4: 2-(4-amino-phenyl)-3H-benzoimidazole-5-carboxylic acid phenylamide was prepared from 2-(4-nitro-phenyl)-3H-benzoimidazole-5-carboxylic acid phenylamide by following the procedure for example 13. MS m/z (M+H) 329.4.

Step 5: 2-{4-[(Oxazole-5-carbonyl)-amino]-phenyl}-1H-benzoimidazole-5-carboxylic acid phenylamide 2-{4-[(Oxazole-2-carbonyl)-amino]-phenyl}-1H-benzoimidazole-5-carboxylic acid phenyl amide was prepared by coupling between 2-(4-amino-phenyl)-1H-benzoimidazole-5-carboxylic acid phenylamide and oxazole-2-carboxylic acid by following the procedure for example 13. $^1$H NMR (400 MHz, DMSO-d6) δ 13.15 (s, 1H), 11.11 (s, 1H), 10.25 (s, 1H), 8.45 (s, 2H), 8.20 (s, 2H), 8.07-8.02 (m, 2H), 7.83 (s, 3H), 7.61 (s, 1H), 7.36 (s, 2H), 7.10 (m, 2H). MS m/z (M+H) 424.1.

Example 15

2-{4-[(Furan-3-carbonyl)-amino]-phenyl}-1H-benzoimidazole-5-carboxylic Acid methyl-phenyl-amide

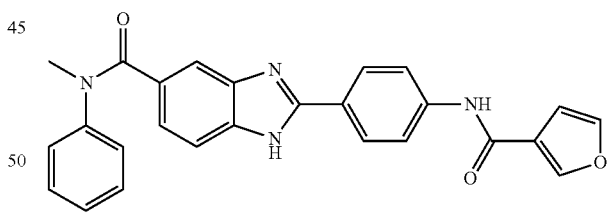

Step 1: 2-(4-nitro-phenyl)-3H-benzoimidazole-5-carboxylic acid methyl-phenyl-amide 2-(4-nitro-phenyl)-3H-benzoimidazole-5-carboxylic acid methyl-phenyl-amide was synthesized using 2-(4-nitro-phenyl)-3H-benzoimidazole-5-carboxylic acid ivb and N-methyl aniline by following the procedure for example 13. MS m/z (M+H) 373.0.

Step 2: 2-(4-amino-phenyl)-3H-benzoimidazole-5-carboxylic acid methyl-phenyl-amide 2-(4-amino-phenyl)-3H-benzoimidazole-5-carboxylic acid methyl-phenyl-amide was prepared from 2-(4-nitro-phenyl)-3H-benzoimidazole-5-carboxylic acid methyl-phenyl-amide by using the procedure for example 13. MS m/z (M+H) 343.1.

Step 3: 2-{4-[(Furan-3-carbonyl)-amino]-phenyl}-1H-benzoimidazole-5-carboxylic acid methyl-phenyl-amide 2-{4-[(Furan-3-carbonyl)-amino]-phenyl}-1H-benzoimidazole-5-carboxylic acid methyl-phenyl-amide was prepared by coupling between 2-(4-amino-phenyl)-1H-benzoimidazole-5-carboxylic acid methyl-phenyl-amide and furan-2-carboxylic acid by following the procedure for example 13. $^1$H NMR (400 MHz, DMSO-d6) δ 13.07 (s, 1H), 10.37 (s, 1H), 8.13-8.05 (m, 2H), 7.97 (d, J=2.0 Hz, 1H), 7.88 (d, J=8.7 Hz, 2H), 7.45-7.30 (m, 4H), 7.29-7.06 (m, 5H), 6.72 (dd, J=3.5, 1.7 Hz, 1H), 3.34 (s, 3H). MS m/z (M+H) 437.0.

Example 16

2-(4-Amino-phenyl)-1H-benzoimidazole-5-carboxylic Acid (3-methoxy-phenyl)-amide

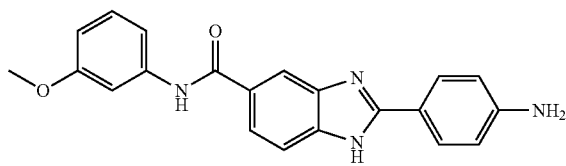 [SMILES: COc1cccc(NC(=O)c2ccc3[nH]c(-c4ccc(N)cc4)nc3c2)c1]

Step 1: 2-(4-nitro-phenyl)-3H-benzoimidazole-5-carboxylic acid (3-methoxy-phenyl)-amide 2-(4-nitro-phenyl)-3H-benzoimidazole-5-carboxylic acid (3-methoxy-phenyl)-amide was synthesized form 2-(4-nitro-phenyl)-1H-benzoimidazole-5-carboxylic acid ivb and 3-chloro-phenylamine by following the procedure for example 13. MS m/z (M+H) 389.0

Step 2: 2-(4-Amino-phenyl)-1H-benzoimidazole-5-carboxylic acid (3-methoxy-phenyl)-amide 2-(4-Amino-phenyl)-1H-benzoimidazole-5-carboxylic acid (3-methoxy-phenyl)-amide was synthesized from 2-(4-nitro-phenyl)-3H-benzoimidazole-5-carboxylic acid (3-methoxy-phenyl)-amide following the procedure for example 13. $^1$H NMR (400 MHz, DMSO-d6) δ 12.71 (d, J=4.2 Hz, 1H), 10.16 (d, J=23.2 Hz, 1H), 8.13 (dd, J=91.8, 1.6 Hz, 1H), 7.92-7.82 (m, 2H), 7.77 (ddd, J=8.4, 2.8, 1.6 Hz, 1H), 7.65-7.49 (m, 2H), 7.46-7.33 (m, 1H), 7.25 (td, J=8.2, 1.8 Hz, 1H), 6.74-6.52 (m, 3H), 5.69 (d, J=11.8 Hz, 2H), 3.76 (s, 3H). MS m/z (M+H) 359.0.

Example 17

2-(4-Amino-phenyl)-1H-benzoimidazole-5-carboxylic Acid Amide

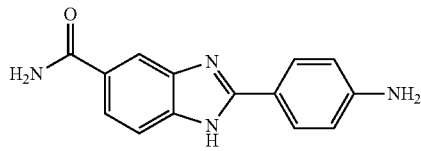 [SMILES: NC(=O)c1ccc2[nH]c(-c3ccc(N)cc3)nc2c1]

Step 1: 2-(4-Nitro-phenyl)-3H-benzoimidazole-5-carboxylic acid amide 2-(4-Nitro-phenyl)-3H-benzoimidazole-5-carboxylic acid amide was synthesized using 3,4-diamino-benzamide xiia and 4-nitro-benzaldehyde by following the procedure for example 1. MS m/z (M+H) 283.1.

Step 2: 2-(4-Amino-phenyl)-1H-benzoimidazole-5-carboxylic acid amide 2-(4-Amino-phenyl)-1H-benzoimidazole-5-carboxylic acid amide was synthesized from 2-(4-Nitro-phenyl)-3H-benzoimidazole-5-carboxylic acid amide following the procedure for example 13. $^1$H NMR (400 MHz, DMSO-d6) δ 12.69 (s, 1H), 8.03 (s, 1H), 7.92 (s, 1H), 7.90-7.83 (m, 2H), 7.69 (dd, J=8.3, 1.7 Hz, 1H), 7.47 (d, J=8.6 Hz, 1H), 7.20 (s, 1H), 6.72-6.63 (m, 2H), 5.67 (s, 2H). MS m/z (M+H) 253.0.

Example 18

2-{4-[(Furan-3-carbonyl)-amino]-phenyl}-1H-benzoimidazole-5-carboxylic Acid Amide

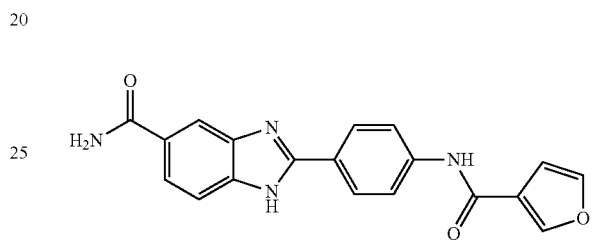

2-{4-[(Furan-3-carbonyl)-amino]-phenyl}-1H-benzoimidazole-5-carboxylic acid amide was synthesized from 2-(4-Amino-phenyl)-1H-benzoimidazole-5-carboxylic acid amide and furan-2-carboxylic acid by following the procedure for example 13. $^1$H NMR (400 MHz, DMSO-d6) δ 13.01 (s, 1H), 10.43 (s, 1H), 8.21-8.11 (m, 3H), 8.01-7.92 (m, 4H), 7.76 (dd, J=8.4, 1.6 Hz, 1H), 7.58 (d, J=8.5 Hz, 1H), 7.40 (d, J=3.4 Hz, 1H), 7.26 (s, 1H), 6.74 (dd, J=3.5, 1.8 Hz, 1H). MS m/z (M−H) 344.8.

Example 19

2-(4-Dimethylamino-phenyl)-1H-benzoimidazole-5-carboxylic Acid (4-chloro-phenyl)-amide

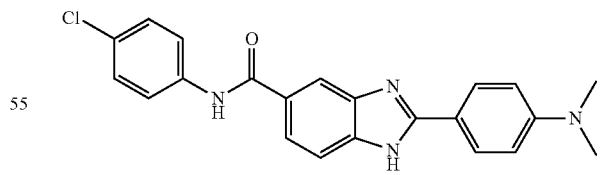

2-(4-Dimethylamino-phenyl)-1H-benzoimidazole-5-carboxylic acid (4-chloro-phenyl)-amide was prepared using 2-(4-dimethylamino-phenyl)-1H-benzoimidazole-5-carboxylic acid and 4-chloroaniline by following the procedure for example 6. $^1$H NMR (400 MHz, DMSO-d6) δ 12.84 (s, 1H), 10.33 (s, 1H), 8.22 (s, 1H), 8.07-7.99 (m, 2H), 7.92-7.83 (m, 2H), 7.79 (dd, J=8.4, 1.7 Hz, 1H), 7.60 (s, 1H), 7.45-7.32 (m, 2H), 6.95-6.80 (m, 2H), 3.01 (s, 6H). MS m/z (M+H) 391.2.

Example 20

2-(4-Dimethylamino-phenyl)-1H-benzoimidazole-5-carboxylic Acid benzothiazol-5-ylamide

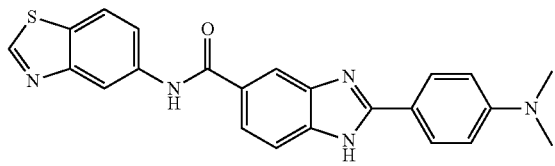 [SMILES: CN(C)c1ccc(-c2nc3cc(C(=O)Nc4ccc5scnc5c4)ccc3[nH]2)cc1]

2-(4-Dimethylamino-phenyl)-1H-benzoimidazole-5-carboxylic acid benzothiazol-5-ylamide was prepared using 2-(4-dimethylamino-phenyl)-1H-benzoimidazole-5-carboxylic acid and 1,3-benzothiazol-5-amine by following the procedure for example 6. $^1$H NMR (400 MHz, DMSO-d6) δ 12.85 (s, 1H), 10.45 (d, J=17.2 Hz, 1H), 9.39 (s, 1H), 8.68 (s, 1H), 8.32 (s, 0.5H), 8.08 (m, 1.5H), 8.04 (d, J=8.8 Hz, 2H), 7.91 (d, J=9.2 Hz, 1H), 7.84 (dd, J=1.6, 8.4 Hz, 1H), 7.60 (m, 1H), 6.86 (d, J=9.2 Hz, 2H), 3.02 (s, 6H). MS m/z (M+H) 413.9.

Example 21

2-(3-Hydroxy-phenyl)-1H-benzoimidazole-5-carboxylic Acid phenethyl-amide

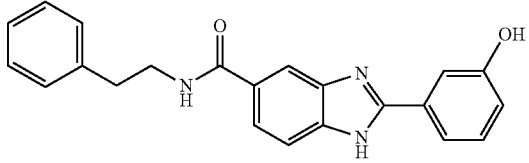 [SMILES: O=C(NCCc1ccccc1)c1ccc2[nH]c(-c3cccc(O)c3)nc2c1]

Step 1: 2-(3-Hydroxy-phenyl)-1H-benzoimidazole-5-carboxylic acid 3,4-Diamino-benzoic acid (0.76 g, 5 mmol) was dissolved in 15 mL of N,N-dimethylformamide and one equivalent of 3-hydroxy-benzaldehyde (0.61 g, 5 mmol) was added. The solution was heated to 80° C. for 5 hours and cooled to room temperature. The precipitate was filtered, washed with methanol and used without further purification (Yield 60%).

Step 2: 2-(3-Hydroxy-phenyl)-1H-benzoimidazole-5-carboxylic acid phenethyl-amide 2-(3-Hydroxy-phenyl)-1H-benzoimidazole-5-carboxylic acid was solubilized in N,N-dimethylformamide at a 0.1 M concentration with 2 equivalents of diisopropylethylamine. The coupling reagent O-(Benzotriazol-1-yl)-N,N,N',N'-tetramethyluronium tetrafluoroborate (TBTU) was solubilized at 0.1 M in N,N-dimethylformamide. One equivalent was added to the acid solution and the reaction mixture was shaken for 5 minutes. Phenethylamine was solubilized in N,N-dimethylformamide at 0.1 M. One equivalent was added to the activated acid solution and the reaction mixture was shaken for 3 hours. The mixture was evaporated and the residue was purified on C18 in a gradient water/methanol with 0.1% ammoniac to afford the final compound as a powder (Yield 75%). MS m/z (M+H) 358.12.

Example 22

2-[4-(5-Methyl-[1,3,4]oxadiazol-2-yl)-phenyl]-1H-benzoimidazole-5-carboxylic Acid

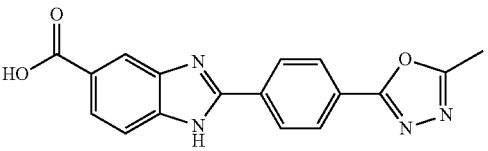 [SMILES: Cc1nnc(-c2ccc(-c3nc4cc(C(=O)O)ccc4[nH]3)cc2)o1]

2-[4-(5-Methyl-[1,3,4]oxadiazol-2-yl)-phenyl]-1H-benzoimidazole-5-carboxylic acid was synthesized from 3,4-diamino-benzoic acid ethyl ester i and 4-(5-methyl-[1,3,4]oxadiazol-2-yl)-benzoic acid by following the procedure for example 26. The hydrolysis of the carboxylic ester occurred during the course of the reaction. $^1$H NMR (400 MHz, DMSO-d6) δ 8.41 (d, J=8.1 Hz, 2H), 8.18 (t, J=10.6 Hz, 3H), 7.87 (d, J=8.3 Hz, 1H), 7.66 (d, J=8.1 Hz, 1H), 2.62 (s, 3H), 1.23 (s, 1H). MS m/z (M+H). 321.0.

Example 23

2-[4-(5-Methyl-[1,3,4]oxadiazol-2-yl)-phenyl]-1H-benzoimidazole-5-carboxylic Acid Phenylamide

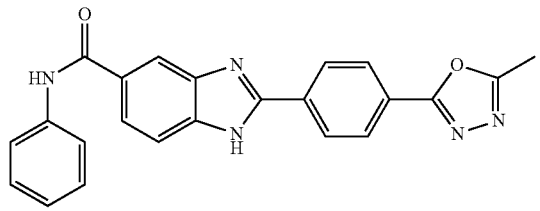 [SMILES: Cc1nnc(-c2ccc(-c3nc4cc(C(=O)Nc5ccccc5)ccc4[nH]3)cc2)o1]

2-[4-(5-Methyl-[1,3,4]oxadiazol-2-yl)-phenyl]-1H-benzoimidazole-5-carboxylic acid phenylamide was synthesized by coupling between 2-[4-(5-methyl-[1,3,4]oxadiazol-2-yl)-phenyl]-1H-benzoimidazole-5-carboxylic acid and aniline using the procedure for example 13. $^1$H NMR (400 MHz, DMSO-d6) δ 10.29 (s, 1H), 8.48-8.39 (m, 2H), 8.22-8.15 (m, 2H), 7.90 (d, J=8.5 Hz, 1H), 7.85-7.79 (m, 2H), 7.74 (s, 1H), 7.36 (t, J=7.9 Hz, 2H), 7.10 (t, J=7.4 Hz, 1H), 2.62 (s, 3H). MS m/z (M+H). 396.0.

Example 24

3-Methyl-3H-imidazole-4-carboxylic Acid [4-(5-benzoyl-1H-benzoimidazol-2-yl)-phenyl]-amide

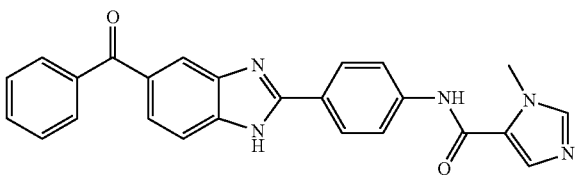 [SMILES: Cn1cncc1C(=O)Nc1ccc(-c2nc3cc(C(=O)c4ccccc4)ccc3[nH]2)cc1]

Step 1: [2-(4-nitro-phenyl)-3H-benzoimidazol-5-yl]-phenyl-methanone

[2-(4-Nitro-phenyl)-3H-benzoimidazol-5-yl]-phenyl-methanone was prepared using (3,4-diamino-phenyl)-phenyl-methanone xiib and 4-nitro-benzaldehyde by following the procedure for example 1. MS m/z (M+H) 344.0.

Step 2: [2-(4-amino-phenyl)-3H-benzoimidazol-5-yl]-phenyl-methanone

[2-(4-amino-phenyl)-3H-benzoimidazol-5-yl]-phenyl-methanone was prepared from [2-(4-nitro-phenyl)-3H-benzoimidazol-5-yl]-phenyl-methanone by following the procedure for example 13. MS m/z (M+H) 313.9.

Step 3: 3-Methyl-3H-imidazole-4-carboxylic acid [4-(5-benzoyl-1H-benzoimidazol-2-yl)-phenyl]-amide 3-Methyl-3H-imidazole-4-carboxylic acid [4-(5-benzoyl-1H-benzoimidazol-2-yl)-phenyl]-amide was synthesized from [2-(4-amino-phenyl)-3H-benzoimidazol-5-yl]-phenyl-methanone and 3-Methyl-3H-imidazole-4-carboxylic acid by following the procedure for example 13. $^1$H NMR (400 MHz, DMSO-d6) δ 13.23 (d, J=22.9 Hz, 1H), 10.30 (s, 1H), 8.21-8.11 (m, 2H), 7.93 (d, J=8.6 Hz, 2H), 7.87 (d, J=7.8 Hz, 2H), 7.80-7.75 (m, 3H), 7.74-7.63 (m, 3H), 7.59 (dd, J=8.2, 6.8 Hz, 2H), 3.88 (s, 3H). MS m/z (M−H) 420.1.

Example 25

Oxazole-2-carboxylic Acid [4-(5-benzoyl-1H-benzoimidazol-2-yl)-phenyl]-amide

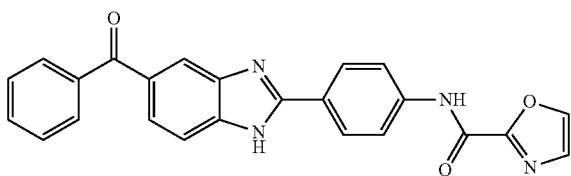 [SMILES: O=C(c1ccccc1)c1ccc2[nH]c(-c3ccc(NC(=O)c4ncco4)cc3)nc2c1]

To a stirred solution of oxazole-2-carboxylic acid (81 mg, 0.718 mmol) in DMF (10 ml) at 25° C., triethylamine (0.35 mL, 1.19 mmol) and PyBOP (303 mg, 0.718 mmol) were added successively and stirred for 15 min. To the above solution, [2-(4-Amino-phenyl)-1H-benzoimidazol-5-yl]-phenyl-methanone (150 mg, 0.479 mmol) was added and the resulting reaction mixture was stirred at 25° C. for 16 h. After completion of the reaction, the reaction mixture was added to ice cold water and extracted with ethyl acetate. The ethyl acetate layer was dried over $Na_2SO_4$ and concentrated under reduced pressure to obtain the crude product which was purified with normal phase column chromatography using silica gel (230-400) in ethyl acetate/hexane solvent to obtain oxazole-2-carboxylic acid [4-(5-benzoyl-1H-benzoimidazol-2-yl)-phenyl]-amide (40 mg, 21% yield). $^1$H NMR (400 MHz, DMSO-d6) δ 13.26 (d, J=24.2 Hz, 1H), 11.14 (s, 1H), 8.46 (s, 1H), 8.19 (d, J=8.6 Hz, 2H), 8.08-7.96 (m, 2H), 7.89 (s, 2H), 7.77 (d, J=7.5 Hz, 2H), 7.73-7.64 (m, 2H), 7.64-7.48 (m, 3H). MS m/z (M+H) 409.1.

Example 26

{2-[4-(5-Methyl-[1,3,4]oxadiazol-2-ylamino)-phenyl]-1H-benzoimidazol-5-yl}-phenyl-methanone

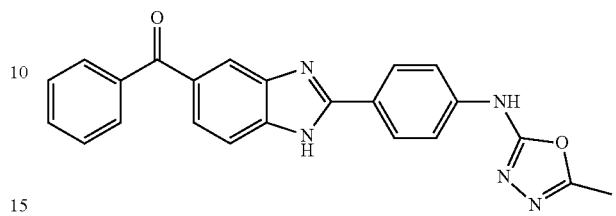

Step 1: 4-(5-Methyl-[1,3,4]oxadiazol-2-ylamino)-benzoic acid ethyl ester 4-(5-Methyl-[1,3,4]oxadiazol-2-ylamino)-benzoic acid ethyl ester was prepared by using Tetrahedron, 2005, 61(22), 5323-5349.

Step 2: 4-(5-Methyl-[1,3,4]oxadiazol-2-ylamino)-benzoic acid 4-(5-Methyl-[1,3,4]oxadiazol-2-ylamino)-benzoic acid was prepared by following the procedure for example 1. MS m/z (M+H) 219.9.

Step 3: {2-[4-(5-Methyl-[1,3,4]oxadiazol-2-ylamino)-phenyl]-1H-benzoimidazol-5-yl}-phenyl-methanone To a reaction vessel containing polyphosphoric acid (5 g) under nitrogen atmosphere at 110° C. (3,4-diamino-phenyl)-phenyl-methanone xiib (175 mg, 0.82 mmol) and 4-(5-Methyl-[1,3,4]oxadiazol-2-ylamino)-benzoic acid (180 mg, 0.82 mmol) were added portion wise. The resulting suspension was heated to 130° C. for 2 h. The reaction was monitored by TLC. After completion of the reaction, the reaction mixture was added to crushed ice and basified with $NaHCO_3$ to pH-9. The resulting suspension was extracted using 20% methanol in $CH_2Cl_2$, organic layer dried over $Na_2SO_4$ and concentrated. The crude product obtained was purified with the help of reverse phase prep HPLC to obtain the product as a pale brown solid 30 mg (9.3%, yield). $^1$H NMR (400 MHz, DMSO-d6) δ 8.21-8.14 (m, 2H), 7.92 (s, 1H), 7.80-7.64 (m, 7H), 7.58 (t, J=7.5 Hz, 2H), 2.43 (s, 3H). MS m/z (M+H) 395.9.

Example 27

{2-[4-(5-Methyl-[1,3,4]oxadiazol-2-yl)-phenyl]-1H-benzoimidazol-5-yl}-phenyl-methanone

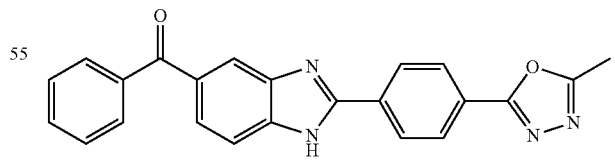

{2-[4-(5-Methyl-[1,3,4]oxadiazol-2-yl)-phenyl]-1H-benzoimidazol-5-yl}-phenyl-methanone was synthesized from 4-(5-methyl-[1,3,4]oxadiazol-2-yl)-benzoic acid (PCT Int. Appl., 2009117676, 24 Sep. 2009) and (3,4-diamino-phenyl)-phenyl-methanone xiib by following the procedure for example 26. $^1$H NMR (400 MHz, DMSO-d6) δ 13.63 (s, 1H), 8.45-8.38 (m, 2H), 8.25-8.12 (m, 2H), 7.99 (s, 1H), 7.78 (dt, J=7.0, 1.4 Hz, 3H), 7.75-7.66 (m, 2H), 7.64-7.51 (m, 2H), 2.62 (s, 3H). MS m/z (M+H) 281.0.

Example 28

Dimethyl-[4-(5-pyrimidin-2-yl-1H-benzoimidazol-2-yl)-phenyl]-amine

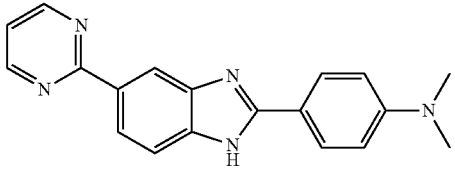 [SMILES: CN(C)c1ccc(-c2nc3cc(-c4ncccn4)ccc3[nH]2)cc1]

Step 1: 4-Pyrimidin-2-yl-benzene-1,2-diamine xiif
4-Pyrimidin-2-yl-benzene-1,2-diamine xiif was prepared by using PCT Int. Appl., 2014176258.

Step 2: Dimethyl-[4-(5-pyrimidin-2-yl-1H-benzoimidazol-2-yl)-phenyl]-amine
Dimethyl-[4-(5-pyrimidin-2-yl-1H-benzoimidazol-2-yl)-phenyl]-amine was synthesized from 4-Pyrimidin-2-yl-benzene-1,2-diamine xiif and 4-dimethylamino-benzaldehyde by following the procedure for example 1. $^1$H NMR (400 MHz, DMSO-d6) δ 12.73 (s, 1H), 8.88 (d, J=4.8 Hz, 2H), 8.52 (s, 1H), 8.27 (d, J=8.5 Hz, 1H), 8.07-7.98 (m, 2H), 7.61 (s, 1H), 7.37 (t, J=4.8 Hz, 1H), 6.92-6.77 (m, 2H), 3.01 (s, 6H). MS m/z (M+H) 316.4.

Example 29

2-Pyridin-4-yl-5-pyrimidin-2-yl-1H-benzoimidazole

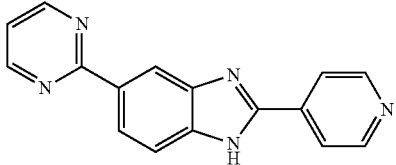 [SMILES: c1cnc(-c2ccc3[nH]c(-c4ccncc4)nc3c2)nc1]

2-Pyridin-4-yl-5-pyrimidin-2-yl-1H-benzoimidazole was synthesized from 4-Pyrimidin-2-yl-benzene-1,2-diamine xiif and pyridine-4-carbaldehyde by following the procedure for example 1. $^1$H NMR (400 MHz, DMSO-d6) δ 13.47 (s, 1H), 8.92 (d, J=4.8 Hz, 2H), 8.83-8.76 (m, 2H), 8.69 (s, 1H), 8.39 (dd, J=8.6, 1.6 Hz, 1H), 8.19-8.09 (m, 2H), 7.78 (d, J=8.4 Hz, 1H), 7.42 (t, J=4.8 Hz, 1H). MS m/z (M+H) 274.1.

Example 30

2-(4-Methylamino-phenyl)-1H-benzoimidazole-5-carbonitrile

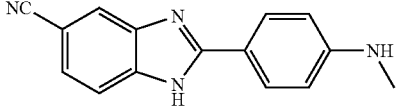 [SMILES: CNc1ccc(-c2nc3cc(C#N)ccc3[nH]2)cc1]

2-(4-Methylamino-phenyl)-1H-benzoimidazole-5-carbonitrile was prepared from 3,4-diamino-benzonitrile xiic and 4-methylamino-benzaldehyde by following the procedure for example 1. $^1$H NMR (400 MHz, DMSO-d6) δ 12.98 (s, 1H), 8.03 (s, 1H), 7.99-7.85 (m, 1H), 7.57 (d, J=8.3 Hz, 1H), 7.50 (d, J=8.6 Hz, 1H), 6.66 (d, J=8.4 Hz, 2H), 6.38-6.30 (m, 1H), 2.75 (d, J=4.9 Hz, 3H). MS m/z (M+H) 248.9.

Example 31

2-(4-Piperidin-1-yl-phenyl)-1H-benzoimidazole-5-carbonitrile

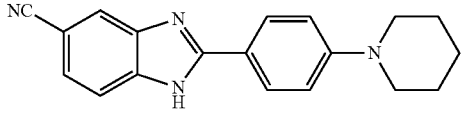 [SMILES: N#Cc1ccc2[nH]c(-c3ccc(N4CCCCC4)cc3)nc2c1]

2-(4-Piperidin-1-yl-phenyl)-1H-benzoimidazole-5-carbonitrile was prepared from 3,4-diamino-benzonitrile xiic and 4-Piperidin-1-yl-benzaldehyde by following the procedure for example 1. $^1$H NMR (400 MHz, DMSO-d6) δ 13.11 (s, 1H), 8.10-7.97 (m, 1H), 8.02 (s, 1H), 7.71 (d, J=8.3 Hz, 1H), 7.60 (d, J=8.3 Hz, 1H), 7.53 (dd, J=8.5, 4.0 Hz, 1H), 7.11-7.03 (m, 2H), 3.86 (m, 4H), 1.60 (t, J=3.2 Hz, 6H). MS m/z (M+H) 303.4.

Example 32

2-(4-Morpholin-4-yl-phenyl)-1H-benzoimidazole-5-carbonitrile

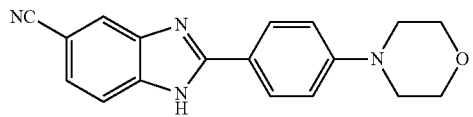 [SMILES: N#Cc1ccc2[nH]c(-c3ccc(N4CCOCC4)cc3)nc2c1]

2-(4-Morpholin-4-yl-phenyl)-1H-benzoimidazole-5-carbonitrile was prepared from 3,4-diamino-benzonitrile xiic and 4-morpholin-4-yl-benzaldehyde by following the procedure for example 1. $^1$H NMR (400 MHz, DMSO-d6) δ 13.17 (s, 1H), 8.06 (d, J=8.7 Hz, 3H), 7.63 (s, 1H), 7.58-7.51 (m, 1H), 7.16-7.08 (m, 2H), 3.76 (t, J=4.9 Hz, 4H), 3.27 (t, J=4.9 Hz, 4H). MS m/z (M+H) 305.3.

Example 33

2-[4-(2-Dimethylamino-ethylamino)-phenyl]-1H-benzoimidazole-5-carbonitrile

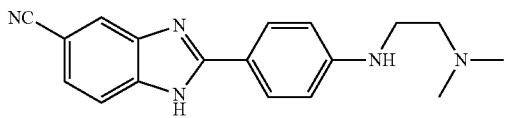 [SMILES: CN(C)CCNc1ccc(-c2nc3cc(C#N)ccc3[nH]2)cc1]

2-[4-(2-Dimethylamino-ethylamino)-phenyl]-1H-benzoimidazole-5-carbonitrile was prepared from 3,4-diamino-benzonitrile xiic and 4-(2-dimethylamino-ethylamino)-benzaldehyde by following the procedure for example 1. $^1$H NMR (400 MHz, DMSO-d6) δ 13.11 (s, 1H), 8.08-7.86 (m, 3H), 7.64 (dd, J=38.3, 8.4 Hz, 1H), 7.51 (d, J=8.5 Hz, 1H), 6.75 (d, J=8.5 Hz, 2H), 6.32 (s, 1H), 3.34-3.24 (m, 2H), 2.79 (d, J=6.9 Hz, 2H), 2.45 (s, 6H). MS m/z (M+H) 306.2.

Example 34

1-Methyl-1H-pyrrole-2-carboxylic acid [4-(5-cyano-1H-benzoimidazol-2-yl)-phenyl]-amide

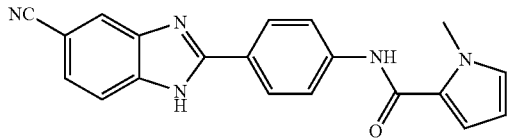 [SMILES: Cn1cccc1C(=O)Nc1ccc(-c2nc3cc(C#N)ccc3[nH]2)cc1]

Step 1: 2-(4-Nitro-phenyl)-1H-benzoimidazole-5-carbonitrile 2-(4-Nitro-phenyl)-1H-benzoimidazole-5-carbonitrile was prepared from 3,4-diamino-benzonitrile xiic and 4-nitro-benzaldehyde by following the procedure for example 1. MS m/z (M−H) 262.9.

Step 2: 2-(4-Amino-phenyl)-1H-benzoimidazole-5-carbonitrile

To a stirred solution of 2-(4-nitro-phenyl)-1H-benzoimidazole-5-carbonitrile (500 mg, 1.89 mmol, 1 eq) in ethanol (20 mL) at 25° C., 5 mL of aqueous solution of $NH_4Cl$ (1.27 g, 22.72 mmol, 12 eq) and iron powder (636 mg, 11.36 mmol, 6 eq) were added and was warmed to 80° C. for 16 h. The reaction was monitored by TLC. After the completion of reaction, the reaction mass was filtered through Celite® bed, the filtrate was concentrated under reduced pressure to obtain a crude product as a brown solid which was further purified by washing with methanol to get 2-(4-amino-phenyl)-1H-benzoimidazole-5-carbonitrile as a reddish brown solid (320 mg, 72% yield). MS m/z (M+H) 234.9.

Step 3: 1-Methyl-1H-pyrrole-2-carboxylic acid [4-(5-cyano-1H-benzoimidazol-2-yl)-phenyl]-amide To a solution of 1-methyl-1H-pyrrole-2-carboxylic acid (240 mg, 1.92 mmol, 1.5 eq) in DMF (10 mL) at 25° C., EDCI (488 mg, 2.56 mmol), 2-(4-amino-phenyl)-1H-benzoimidazole-5-carbonitrile (400 mg, 1.28 mmol) and DMAP (35 mg, 0.25 mmol) were added. The resulting reaction mass warmed to 80° C. for 16 hrs. Reaction was monitored by TLC. After completion of reaction, the reaction mixture from above was added to crushed ice, filtered and the solid obtained from above was purified by column chromatography using silica gel 230-400 in $CH_2Cl_2$/methanol solvent system. The product obtained was further purified by recrystallization from methanol to obtain 1-methyl-1H-pyrrole-2-carboxylic acid [4-(5-cyano-1H-benzoimidazol-2-yl)-phenyl]-amide as an off white solid (95 mg, 16% yield). $^1H$ NMR (400 MHz, DMSO-d6) δ 13.36 (s, 1H), 10.01 (s, 1H), 8.16 (d, J=7.6 Hz, 2H), 7.98-7.90 (m, 2H), 7.78 (s, 1H), 7.67 (s, 1H), 7.58 (d, J=8.5 Hz, 1H), 7.13-7.02 (m, 2H), 6.13 (dd, J=4.0, 2.5 Hz, 1H), 3.90 (s, 3H). MS m/z (M+H) 342.1.

Example 35

N-[4-(5-Cyano-1H-benzoimidazol-2-yl)-phenyl]-4-methoxy-benzamide

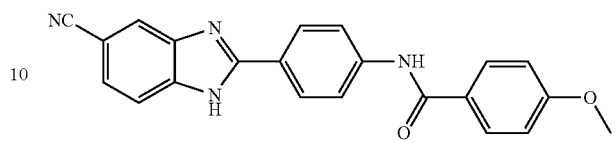

N-[4-(5-Cyano-1H-benzoimidazol-2-yl)-phenyl]-4-methoxy-benzamide was prepared from 4-methoxybenzoic acid and 2-(4-amino-phenyl)-1H-benzoimidazole-5-carbonitrile by following the procedure for example 34. $^1H$ NMR (400 MHz, DMSO-d6) δ 10.23 (s, 1H), 8.21 (d, J=8.4 Hz, 2H), 7.99 (d, J=8.4 Hz, 2H), 7.87 (d, J=8.1 Hz, 3H), 7.55 (d, J=8.2 Hz, 1H), 7.28 (d, J=8.1 Hz, 1H), 7.08 (d, J=8.4 Hz, 2H), 3.85 (s, 3H). MS m/z (M+H) 369.1.

Example 36

2-[4-(2-Morpholin-4-yl-2-oxo-ethoxy)-phenyl]-1H-benzoimidazole-5-carbonitrile

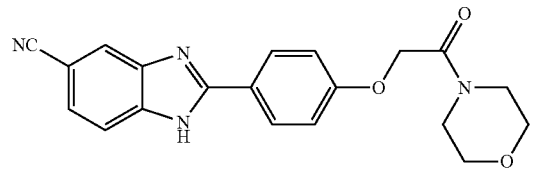 [SMILES: N#Cc1ccc2[nH]c(-c3ccc(OCC(=O)N4CCOCC4)cc3)nc2c1]

2-[4-(2-Morpholin-4-yl-2-oxo-ethoxy)-phenyl]-1H-benzoimidazole-5-carbonitrile was prepared from 4-(2-Morpholin-4-yl-2-oxo-ethoxy)-benzaldehyde (prepared by using J. Med. Chem. 2014, 57(13), 5579-5601) and 3,4-diamino-benzonitrile xiic by following the procedure for example 1. $^1H$ NMR (400 MHz, DMSO-d6) δ 13.30 (s, 1H), 8.13 (d, J=8.6 Hz, 3H), 7.72 (d, J=39.4 Hz, 1H), 7.57 (d, J=8.4 Hz, 1H), 7.16-7.09 (m, 2H), 4.97 (s, 2H), 3.61 (dt, J=20.9, 4.7 Hz, 4H), 3.48 (dd, J=9.0, 4.8 Hz, 4H). MS m/z (M+H) 363.1.

Example 37

N,N-Dimethyl-N'-[4-(5-trifluoromethyl-1H-benzoimidazol-2-yl)-phenyl]-ethane-1,2-diamine

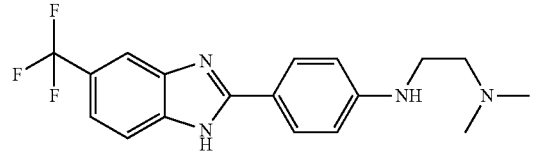 [SMILES: CN(C)CCNc1ccc(-c2nc3cc(C(F)(F)F)ccc3[nH]2)cc1]

N,N-Dimethyl-N'-[4-(5-trifluoromethyl-1H-benzoimidazol-2-yl)-phenyl]-ethane-1,2-diamine was prepared from 4-(trifluoromethyl)benzene-1,2-diamine xiih and 4-(2-dimethylamino-ethylamino)-benzaldehyde by following the procedure for example 1. $^1H$ NMR (400 MHz, DMSO-d6)

δ 12.88 (s, 1H), 7.92 (d, J=8.4 Hz, 1H), 7.87 (s, 1H), 7.76-7.67 (m, 1H), 7.60 (d, J=8.3 Hz, 1H), 7.43 (d, J=8.4 Hz, 1H), 6.73 (d, J=8.4 Hz, 2H), 6.14-6.03 (m, 1H), 3.19 (q, J=6.2 Hz, 2H), 2.47 (d, J=6.7 Hz, 2H), 2.21 (s, 6H). MS m/z (M+H) 349.0.

Example 38

Furan-3-carboxylic Acid [4-(5-trifluoromethyl-1H-benzoimidazol-2-yl)-phenyl]-amide

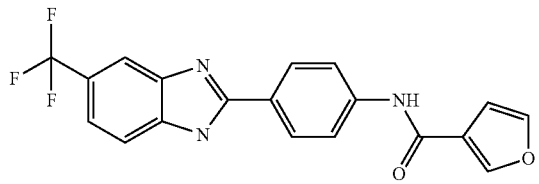

Step 1: 2-(4-nitrophenyl)-5-(trifluoromethyl)-1H-benzoimidazole
2-(4-nitrophenyl)-5-(trifluoromethyl)-1H-benzoimidazole was synthesized from 4-(trifluoromethyl)benzene-1,2-diamine xiih and 4-nitro-benzaldehyde by following the procedure for example 1. MS m/z (M+H) 308.0.

Step 2: 4-[5-(trifluoromethyl)-1H-benzoimidazol-2-yl]aniline
4-[5-(trifluoromethyl)-1H-benzoimidazol-2-yl]aniline was synthesized from 2-(4-nitrophenyl)-5-(trifluoromethyl)-1H-benzoimidazole by following the procedure for example 34. $^1$H NMR (400 MHz, DMSO-d6) δ 12.84 (s, 1H), 7.91-7.83 (m, 2H), 7.67 (t, J=19.9 Hz, 2H), 7.43 (dd, J=8.4, 1.7 Hz, 1H), 6.74-6.64 (m, 2H), 5.72 (s, 2H). MS m/z (M+H) 278.0.

Step 3: Furan-3-carboxylic acid [4-(5-trifluoromethyl-1H-benzoimidazol-2-yl)-phenyl]-amide
Furan-3-carboxylic acid [4-(5-trifluoromethyl-1H-benzoimidazol-2-yl)-phenyl]-amide was synthesized from 4-[5-(trifluoromethyl)-1H-benzoimidazol-2-yl]aniline and furan-3-carboxylic acid by following the procedure for example 13. $^1$H NMR (400 MHz, DMSO-d6) δ 10.45 (s, 1H), 8.52 (d, J=1.4 Hz, 1H), 8.30 (d, J=8.5 Hz, 2H), 8.10-8.02 (m, 3H), 7.92 (d, J=8.5 Hz, 1H), 7.84 (t, J=1.7 Hz, 1H), 7.73 (d, J=8.7 Hz, 1H), 7.06 (d, J=1.9 Hz, 1H). MS m/z (M+H) 372.1.

Example 39

Furan-3-carboxylic Acid (2-pyridin-4-yl-1H-benzoimidazol-5-yl)-amide

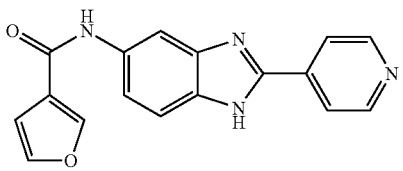 [SMILES: O=C(Nc1ccc2[nH]c(-c3ccncc3)nc2c1)c1ccoc1]

Step 1: 5-nitro-2-(pyridin-4-yl)-1H-benzoimidazole
5-nitro-2-(pyridin-4-yl)-1H-benzoimidazole was synthesized from 4-nitro-benzene-1,2-diamine xiig and pyridine-4-carbaldehyde by following the procedure for example 1. MS m/z (M+H) 241.0.

Step 2: 2-(pyridin-4-yl)-1H-benzoimidazol-5-amine
2-(pyridin-4-yl)-1H-benzoimidazol-5-amine was synthesized from 5-nitro-2-(pyridin-4-yl)-1H-benzoimidazole by following the procedure for example 34. MS m/z (M+H) 211.1.

Step 3: Furan-3-carboxylic acid (2-pyridin-4-yl-1H-benzoimidazol-5-yl)-amide
Furan-3-carboxylic acid (2-pyridin-4-yl-1H-benzoimidazol-5-yl)-amide was synthesized using 2-(pyridin-4-yl)-1H-benzoimidazol-5-amine and furan-3-carboxylic acid by following the procedure for example 13. $^1$H NMR (400 MHz, DMSO-d6) δ 13.22 (d, J=18.4 Hz, 1H), 10.27 (d, J=30.2 Hz, 1H), 8.81-8.69 (m, 2H), 8.31-8.14 (m, 1H), 8.07 (dd, J=12.4, 5.3 Hz, 2H), 7.95 (d, J=4.2 Hz, 1H), 7.66 (dd, J=15.6, 8.3 Hz, 1H), 7.60-7.46 (m, 1H), 7.35 (dd, J=9.5, 3.5 Hz, 1H), 6.72 (q, J=2.7 Hz, 1H). MS m/z (M+H) 305.0.

Example 40

N'-[4-(4,6-Dimethyl-1H-benzoimidazol-2-yl)-phenyl]-N,N-dimethyl-ethane-1,2-diamine

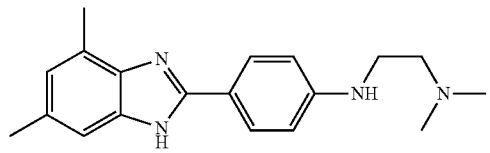

N'-[4-(4,6-Dimethyl-1H-benzoimidazol-2-yl)-phenyl]-N,N-dimethyl-ethane-1,2-diamine was synthesized from 3,5-dimethyl-benzene-1,2-diamine xiid and 4-(2-dimethylamino-ethylamino)-benzaldehyde by following the procedure for example 1. $^1$H NMR (400 MHz, DMSO-d6) δ 12.19 (s, 1H), 7.93 (d, J=8.4 Hz, 1H), 7.86 (d, J=8.7 Hz, 1H), 7.02 (s, 1H), 6.76-6.65 (m, 3H), 5.87 (d, J=3.9 Hz, 1H), 3.16 (q, J=6.4 Hz, 2H), 2.51-2.42 (m, 5H), 2.35 (d, J=7.6 Hz, 3H), 2.20 (s, 6H). MS m/z (M+H) 309.2.

Example 41

[4-(6-Chloro-4-methyl-1H-benzoimidazol-2-yl)-phenyl]-dimethyl-amine

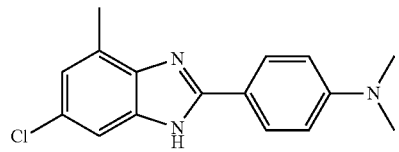 [SMILES: Cc1cc(Cl)cc2[nH]c(-c3ccc(N(C)C)cc3)nc12]

[4-(6-Chloro-4-methyl-1H-benzoimidazol-2-yl)-phenyl]-dimethyl-amine was synthesized from 5-chloro-3-methyl-benzene-1,2-diamine xiie and 4-4-dimethylamino-benzaldehyde by following the procedure for example 1. $^1$H NMR (400 MHz, DMSO-d6) δ 12.49 (d, J=90.9 Hz, 1H), 8.05 (d, J=8.6 Hz, 1H), 7.97 (d, J=8.6 Hz, 1H), 7.55-7.19 (m, 1H), 6.97 (s, 1H), 6.83 (d, J=8.4 Hz, 2H), 3.00 (d, J=1.8 Hz, 6H), 2.55 (s, 3H). MS m/z (M+H) 286.1.

Example 42

Furan-3-carboxylic Acid [4-(6-chloro-4-methyl-1H-benzoimidazol-2-yl)-phenyl]-amide

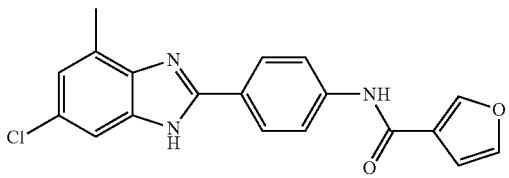 [SMILES: Cc1cc(Cl)cc2[nH]c(-c3ccc(NC(=O)c4ccoc4)cc3)nc12]

Step 1: 6-chloro-4-methyl-2-(4-nitrophenyl)-1H-benzoimidazole
6-chloro-4-methyl-2-(4-nitrophenyl)-1H-benzoimidazole was synthesized from 5-chloro-3-methyl-benzene-1,2-diamine xiie and 4-nitro benzaldehyde by following the procedure for example 1. MS m/z (M+H) 288.1.

Step 2: 4-(6-chloro-4-methyl-1H-benzoimidazol-2-yl) aniline
4-(6-chloro-4-methyl-1H-benzoimidazol-2-yl)aniline was synthesized from 6-chloro-4-methyl-2-(4-nitrophenyl)-1H-benzoimidazole by following the procedure for example 34. MS m/z (M+H) 258.1.

Step 3: Furan-3-carboxylic acid [4-(6-chloro-4-methyl-1H-benzoimidazol-2-yl)-phenyl]-amide
Furan-3-carboxylic acid [4-(6-chloro-4-methyl-1H-benzoimidazol-2-yl)-phenyl]-amide was synthesized from 4-(6-chloro-4-methyl-1H-benzoimidazol-2-yl)aniline and furan-3-carboxylic acid by following the procedure for example 13. $^1$H NMR (400 MHz, DMSO-d6) δ 12.80 (d, J=91.6 Hz, 1H), 10.15 (s, 1H), 8.43 (t, J=1.1 Hz, 1H), 8.21 (d, J=8.5 Hz, 1H), 8.14 (d, J=8.5 Hz, 1H), 7.91 (d, J=8.5 Hz, 2H), 7.83 (t, J=1.8 Hz, 1H), 7.52-7.31 (m, 2H), 7.03 (d, J=2.1 Hz, 1H), 2.58-2.55 (m, 3H). MS m/z (M+H) 352.1.

Example 43

Furan-2-yl-[4-(1H-imidazo[4,5-c]pyridin-2-yl)-phenyl]-methanone

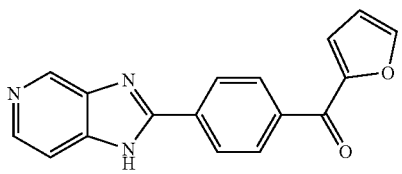 [SMILES: O=C(c1ccc(-c2nc3cnccc3[nH]2)cc1)c1ccco1]

Step 1: 4-(furan-2-carbonyl)-benzoic acid
4-(Furan-2-carbonyl)-benzoic acid was synthesized from 4-(furan-2-carbonyl)-benzoic acid methyl ester (synthesized as per Eur. J. Org. Chem. 2011, 14, 2662-2667) by following the procedure for example 1. MS m/z (M−H) 215.1.

Step 2: Furan-2-yl-[4-(1H-imidazo[4,5-c]pyridin-2-yl)-phenyl]-methanone
Furan-2-yl-[4-(1H-imidazo[4,5-c]pyridin-2-yl)-phenyl]-methanone was synthesized from 4-(furan-2-carbonyl)-benzoic acid and pyridine-3,4-diamine by following the procedure for example 26. $^1$H NMR (400 MHz, DMSO-d6) δ 13.63 (s, 1H), 9.01 (s, 1H), 8.44-8.31 (m, 3H), 8.20-8.06 (m, 3H), 7.65 (d, J=5.6 Hz, 1H), 7.50 (d, J=3.6 Hz, 1H), 6.84 (dd, J=3.6, 1.7 Hz, 1H). MS m/z (M+H). 290.0.

Example 44

N-(6-Acetyl-benzo[1,3]dioxol-5-yl)-2-[3-(1H-benzoimidazol-2-yl)-piperidin-1-yl]-acetamide

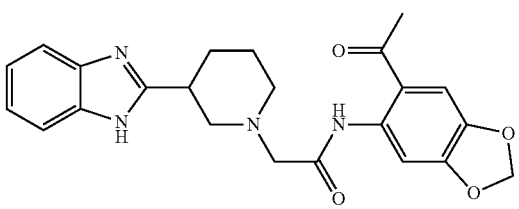 [SMILES: CC(=O)c1cc2c(cc1NC(=O)CN1CCCC(c3nc4ccccc4[nH]3)C1)OCO2]

Step 1: 2-Piperidin-3-yl-1H-benzoimidazole
1-(6-Amino-benzo[1,3]dioxol-5-yl)-ethanone (0.90 g, 5 mmol) was dissolved in tetrahydrofuran (50 mL) with one equivalent of triethylamine (0.50 g, 5 mmol). Chloroacetyl chloride (0.56 g, 5 mmol) was added dropwise and the mixture was stirred for one hour and evaporated. The residue was dissolved in ethyl acetate and washed with water. The organic layer was dried over magnesium sulfate and evaporated to afford a solid that was used without further purification. (Yield 95%).

Step 2: N-(6-Acetyl-benzo[1,3]dioxol-5-yl)-2-[3-(1H-benzoimidazol-2-yl)-piperidin-1-yl]-acetamide
2-Piperidin-3-yl-1H-benzoimidazole was solubilized in N,N-dimethylformamide at a 0.1 M concentration with 2 equivalents of diisopropylethylamine. N-(6-Acetyl-benzo[1,3]dioxol-5-yl)-2-chloro-acetamide was solubilized in N,N-dimethylformamide at a 0.1 M. One equivalent was added to the amine solution and the reaction mixture was heated at 80° C. for 8 hours. The mixture was evaporated and the residue was purified on C18 in a gradient water/methanol with 0.1% ammoniac to afford the final compound as a powder (Yield 80%). MS m/z (M+H). 421.15.

Example 45

2-(4-Dimethylamino-phenyl)-1H-benzoimidazole-5-carboxylic Acid Phenyl Amide

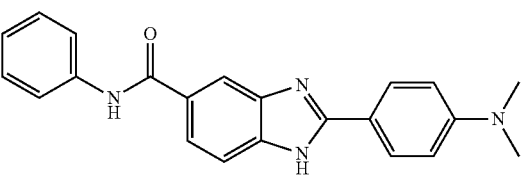

2-(4-Dimethylamino-phenyl)-1H-benzoimidazole-5-carboxylic acid phenyl amide was synthesized from 2-(4-dimethylamino-phenyl)-1H-benzoimidazole-5-carboxylic acid and aniline by following the procedure for example 1. $^1$H NMR (400 MHz, DMSO-d6) δ 12.81 (s, 1H), 10.19 (s, 1H), 8.27 (s, 1H), 8.08-8.00 (m, 2H), 7.86-7.77 (m, 3H), 7.59 (d, J=33.0 Hz, 1H), 7.39-7.31 (m, 2H), 7.13-7.03 (m, 1H), 6.90-6.82 (m, 2H), 3.02 (s, 6H). MS m/z (M+H) 357.1.

Example 46

2-(4-dimethylamino-phenyl)-1H-benzoimidazole-5-carboxylic Acid (3-chloro-phenyl)-amide

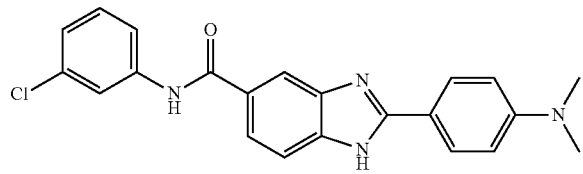

2-(4-dimethylamino-phenyl)-1H-benzoimidazole-5-carboxylic acid (3-chloro-phenyl)-amide was synthesized from 2-(4-dimethylamino-phenyl)-1H-benzoimidazole-5-carboxylic acid and 3-chloro-phenylamine by following the procedure for example 1. $^1$H NMR (400 MHz, DMSO-d6) δ 12.90 (s, 1H), 10.37 (s, 1H), 8.17 (s, 1H), 8.08-7.98 (m, 3H), 7.82-7.73 (m, 2H), 7.61 (d, J=8.3 Hz, 1H), 7.39 (t, J=8.1 Hz, 1H), 7.15 (ddd, J=8.0, 2.1, 0.9 Hz, 1H), 6.91-6.81 (m, 2H), 3.02 (s, 6H). MS m/z (M+H) 390.9.

2/Biological Activity 2-1/In Vitro Determination of Compound Activity by HRTF Assay Principle:

In the experiment, recombinant Erk1 and Erk2, tagged with a polyhistidine stretch in their N-terminal part were used. To reproduce the interaction between ERK1/2 and Myd88, a peptide corresponding to amino acids 24-40 of Myd88 was used: biotin-Ahx-PLAALNMRVRRRLSLFLNVR with Ahx being aminohexanoic acid as a spacer (biotin-MyD88peptide). This peptide encompassed the interaction motif of Myd88 with the CD domain of ERK1/2. To perform the HTRF assay this peptide was N-terminally labelled with biotin. To detect the interaction between the peptide and Erk1 or Erk2 the following components were used: an antibody directed against the His-tag, labelled with the donor fluorophore (Europium cryptate); The streptavidine protein, labelled with the acceptor XL665 fluorophore directed against the biotin. All the components except Erk1, Erk2 and the peptide were purchased from Cisbio (Condolet, France).

Homogeneous Time Resolved Fluorescence (HTRF) assay combines two techniques: Fluorescence Resonance Energy Transfer (FRET) and Time Resolved (TR) measurement. In TR-FRET, a transfer of fluorescence between a donor and an acceptor molecule generates a signal that can then be measured. This energy transfer is only possible when both fluorophores are close enough to each other. Therefore, this method can be used to detect protein-protein interaction.

Experimentation:

For MyD88-ERK1 interaction the reaction medium contained: 6×His-ERK1 at 7.5 nM, biotin-MyD88peptide at 25 nM, anti-Histidine-Cryptate antibody at 1.3325 nM and XL665 labeled-Streptavidine at 3.125 nM.

For MyD88-ERK2 interaction the reaction medium contained: GST-ERK2 at 50 nM, biotin-MyD88pep at 50 nM, anti-GST-Cryptate antibody at 0.8 nM and XL665 labeled-Streptavidine at 12.5 nM.

Concentrations of compounds to be tested ranged from 0.1 µM to 100 µM. Stock solutions of compounds according to the invention were prepared at 10 mM in DMSO. Compounds stock solution were directly distributed in black 384-well plate (Greiner low-volume) in Tris-HCl 20 mM, pH 8/0.1% BSA/0.05% Tween 20/150 mM NaCl (ERK1 assay) or in Tris-HCl 10 mM, pH8/0.1% BSA/0.05% Tween 20/150 mM NaCl (ERK2 assay) by an HP D300 Digital Dispenser to obtain the required final concentrations. Proteins (ERK1, ERK2) were then added and the plate was incubated for 30 min at room temperature. After incubation, biotin-Myd88peptide, anti-his-K, anti-GST-k and XL665-Streptavidin were added to each corresponding well to reach a final volume of 20 µL. The plate was incubated at room temperature for 2 hours and fluorescence was measured using a TECAN Infinite F500 Reader®.

Results are calculated as the variation of fluorescence (Delta F) between control and samples. Delta F was calculated using the following equation: [(Ratio sample−Ratio of the arithmetic mean of the control)/Ratio of the arithmetic mean of the control]×100 where ratio=(Acceptor fluorescence/Donor fluorescence)×10000. The IC50 were determinated using GraphPad software following this equation: log (inhibitor) versus response variable slope (jour parameters) y=Bottom+[(Top−Bottom)/(1+10((log IC50−X) hillslope)]. Bottom was determinated by the equation and Top was the DMSO control value. The results are presented below at paragraph 2-5.

2-2/Cell-Based Assay

The terms "SRE promoter" refer to "Serum response elements", which is a DNA sequence (CC(A/T)6GG) that is used upstream of reporter genes and is known to be the binding site of the SRF (Serum response factor) proteins encoded by SRF gene identified by Gene Bank number (Gene ID: 6722, NM_003131.2). To determine the activity of the compounds on ERK1/2, Fluman Colon Tumor (HCT116) p53+/+ cell line stably transformed to express the luciferase reporter gene under the control of the serum response element (SRE) was used. This cell line was cultured in McCoy's medium supplemented with 10% FBS, 2 mM glutamine, 1% antibiotics and 1 µM of puromycin.

HCT116 p53+/+ SRE luciferase cells were plated in 96-well flat-bottom plate at 20,000/well and incubated at 37° C. for 36 hours. The medium was discarded and replaced by 100 µl of serum free medium for 16 hours. Cells were then pretreated for 2 hours with the compounds according to the invention at various concentrations (from 0.001 µM to 80 µM). Cells were then stimulated by addition of 10% FCS and incubated at 37° C. for four additional hours and the expression of reporter gene was assessed using the One-Glo Luciferase reagent (Promega). Luminescence was quantified after 5 minutes in a TECAN infinite M200 Reader (Männedorf, Switzerland). The results are presented below at paragraph 2-5.

2-3/Apoptosis Assay

Figure 2:
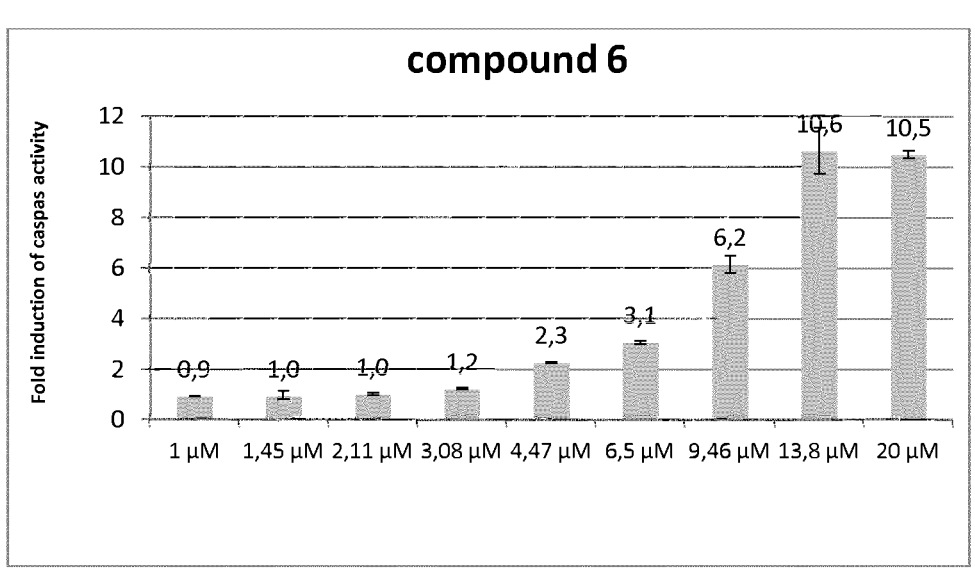
Figure 3:
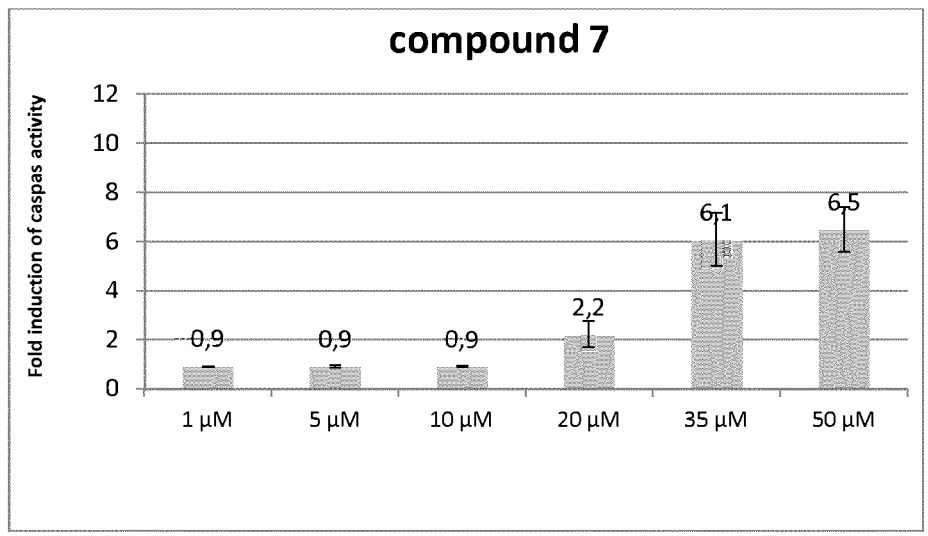

Cellular apoptosis was measured using the Caspase-Glo® 3/7 assay kit (Promega). To perform this study, HCT116 p53+/+ cells were seeded at a density of 7,000 cell/well in 96-half wells plate and maintained 24 h at 37° C. in McCoy's medium supplemented with 2 mM glutamine, 1% penicillin, 1% of streptomycin and 10% FBS. Cells were then treated with the compounds at various concentrations ranging from 1 µM to 100 µM depending on the compound. The DMSO concentration was normalized at 1% in each well and the cells were incubated for 16 h. Caspase 3/7 activity was monitored using caspase-Glo 3/7 kit according to the manufacturer instructions. Briefly, 50 µL of Caspase-Glo® 3/7 reagent was added in each well and the plates were gently agitated for 30 s and let at room temperature for an additional hour. Luminescence was then measured in a TECAN infinite 200 microplate reader. Results are expressed as the fold induction of caspase 3/7 activation using DMSO treated cells as control. The results are presented on FIGS. 1 to 3.

2-4/Xenograft

Figure 4:
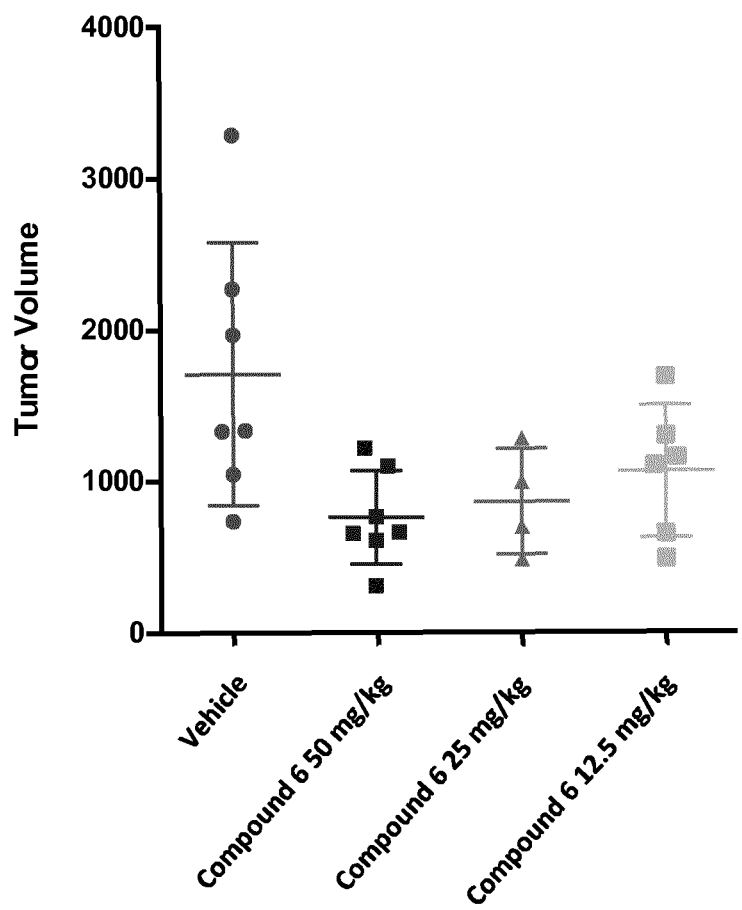
FIG. 4 shows the xenograft results on mice treated with compound 6 or vehicle.

HCT116 cells were subcutaneously injected into the flank of 6-week-old female Swiss-nude mice (Charles River, Les Oncins, France). When tumors reached 100 mm³, mice were treated intraperitoneally daily with 50, 25, 12.5 mg/kg of compound 6, or a vehicle. Tumor volume was measured twice a week with an electronic caliper. The results are presented on FIG. 4.

2-5/Results

| Compounds | IC50* (µM) on Myd88-ERK1 in HRTF Assay | IC50* (µM) on Myd88-ERK2 in HRTF Assay | IC50* (µM) in cell-based Assay |
|---|---|---|---|
| 6 | 4.44 | 2.34 | 0.48 |
| 2 | 8 | 11.76 | 0.32 |
| 7 | 6.15 | 25.5 | 0.79 |
| Comp. ex.** | >50 (Inactive) | >50 (Inactive) | >50 (Inactive) |

*Inhibition Concentration: the concentration providing 50% of inhibition,

**Comp. ex. =

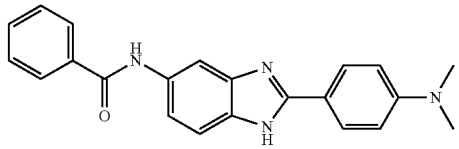

The smaller is the IC50 value, the higher is the inhibition, the better is the activity of the compounds.

The invention claimed is:

1. A method of treatment of cancer comprising the administration to a person in need thereof an effective amount of a compound of the following formula (I'), a pharmaceutically acceptable salt thereof, a stereoisomer or a mixture of stereoisomers thereof, in any proportions:

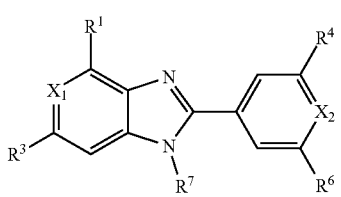

(I')

wherein:
  $X_1$ represents $CR^2$;
  $X_2$ represents $CR^5$;
  $R^1$ represents H, (C1-C6)alkyl or halogen;
  $R^2$ represents CONR11R12; wherein
    R11 represents H or (C1-C6)alkyl;
    R12 represents a (C1-C6)alkyl, aryl, aryl-(C1-C6)alkyl or 5- or 6-membered heteroaryl group optionally substituted with one or more groups selected from halo, (C1-C6)alkyl, OR35 and NR36R37;
    R35, R36, and R37 represent, independently of one another, H or (C1-C6)alkyl;
  $R^3$ represents H, (C1-C6)alkyl or halogen;
  $R^4$ represents H, Cl, CN, NO$_2$, NHR18 or OR19, wherein:
    R18 represents H, (C1-C6)alkyl, aryl, heteroaryl or (C1-C6)alkylcarbonyl;
    R19 represents H or (C1-C6)alkyl;
  $R^5$ represents NR21R22 wherein:
    R21 represents H or R41;
    R22 represents H or R42;
    or R21 and R22 form together with the nitrogen atom bearing them a heterocycle optionally substituted with a (C1-C6)alkyl group;
    R41 and R42 represent, independently of one another, a (C1-C6)alkyl, aryl, aryl-(C1-C6)alkyl or heteroaryl group optionally substituted with one or more groups selected from halo, (C1-C6) alkyl, OR43 and NR44R45;
    R43, R44 and R45 represent, independently of one another, H or (C1-C6)alkyl;
  $R^6$ represents H, OH, (C1-C6)alkoxy or (C1-C6)alkyl; and
  $R^7$ represents H or (C1-C6)alkyl; and
    wherein the cancer is lung cancer, colon cancer, colorectal cancer, head and neck cancer, prostate cancer, breast cancer, ovarian cancer, cervical cancer, leukemia, lymphoid cancer, skin cancer, pancreatic cancer, intestinal cancer, liver cancer, bladder cancer, esophageal cancer, gastric cancer, male genital cancer, mesothelioma, sarcoma, or bone cancer.

2. A method for inhibiting oncogenesis and/or cancer cell growing through the MyD88/ERK cell pathway, and/or for stimulating the display of immunogenic cell death (ICD) markers on the cell membrane of cancer cells comprising the administration to a person in need thereof an effective amount of a compound of following formula (I'), a pharmaceutically acceptable salt thereof, a stereoisomer or a mixture of stereoisomers thereof, in any proportions:

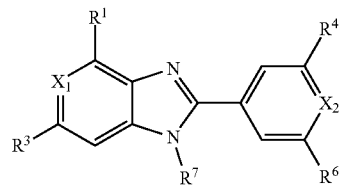

(I')

wherein:
  $X_1$ represents $CR^2$;
  $X_2$ represents $CR^5$;
  $R^1$ represents H, (C1-C6)alkyl or halogen;
  $R^2$ represents CONR11R12; wherein
    R11 represents H or (C1-C6)alkyl;
    R12 represents a (C1-C6)alkyl, aryl, aryl-(C1-C6) alkyl or 5- or 6-membered heteroaryl group optionally substituted with one or more groups selected from halo, (C1-C6)alkyl, OR35 and NR36R37;
    R35, R36, and R37 represent, independently of one another, H or (C1-C6)alkyl;
  $R^3$ represents H, (C1-C6)alkyl or halogen;
  $R^4$ represents H, Cl, CN, NO$_2$, NHR18 or OR19, wherein:
    R18 represents H, (C1-C6)alkyl, aryl, heteroaryl or (C1-C6)alkylcarbonyl;
    R19 represents H or (C1-C6)alkyl;
  $R^5$ represents NR21R22 wherein:
    R21 represents H or R41;
    R22 represents H or R42;

or R21 and R22 form together with the nitrogen atom bearing them a heterocycle optionally substituted with a (C1-C6)alkyl group;

R41 and R42 represent, independently of one another, a (C1-C6)alkyl, aryl, aryl-(C1-C6)alkyl or heteroaryl group optionally substituted with one or more groups selected from halo, (C1-C6)alkyl, OR43 and NR44R45;

R43, R44 and R45 represent, independently of one another, H or (C1-C6)alkyl;

R6 represents H, OH, (C1-C6)alkoxy or (C1-C6)alkyl; and

R7 represents H or (C1-C6)alkyl.

3. The method according to claim 2, wherein the compound of formula (I') is selected from:

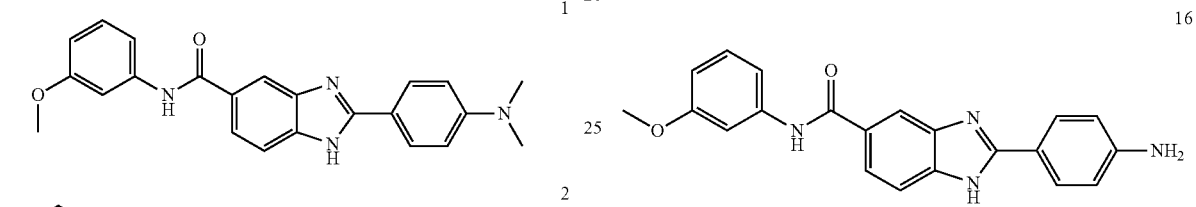

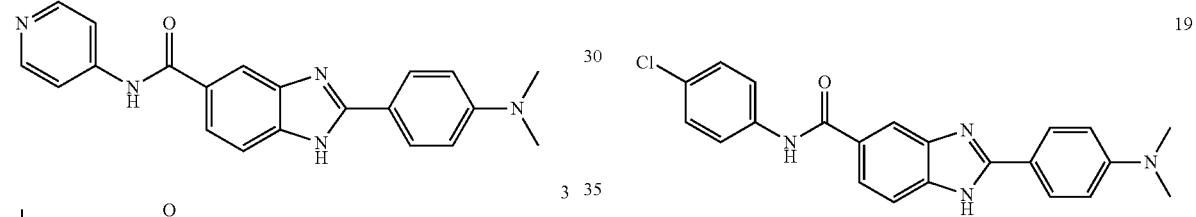

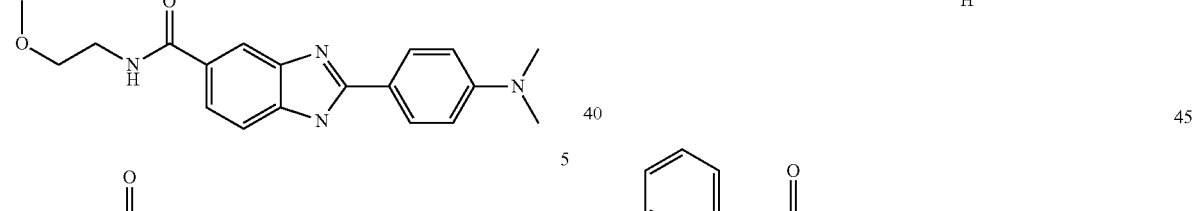

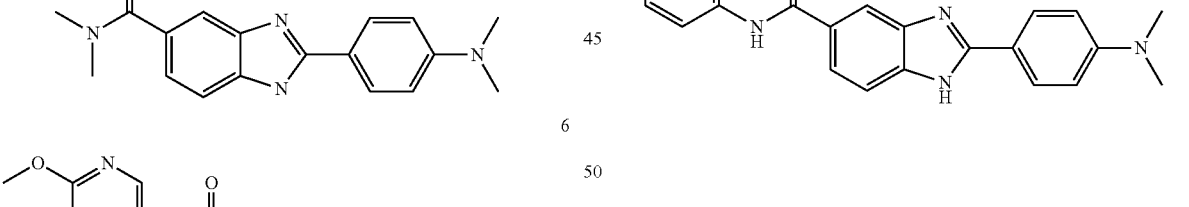

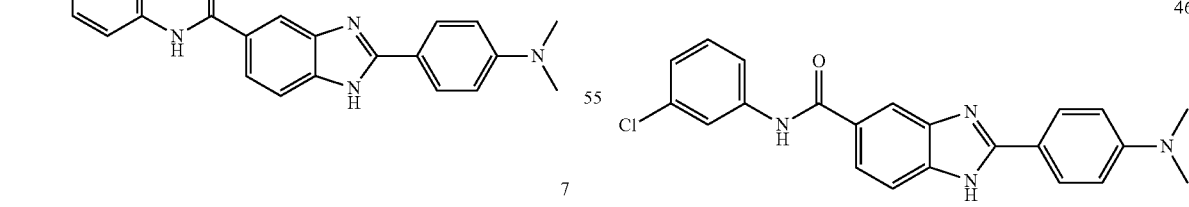

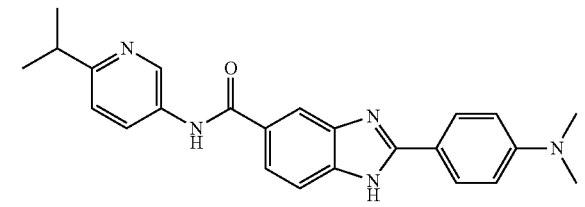

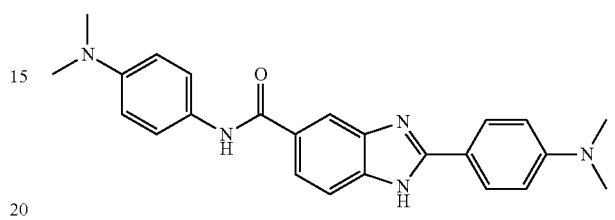

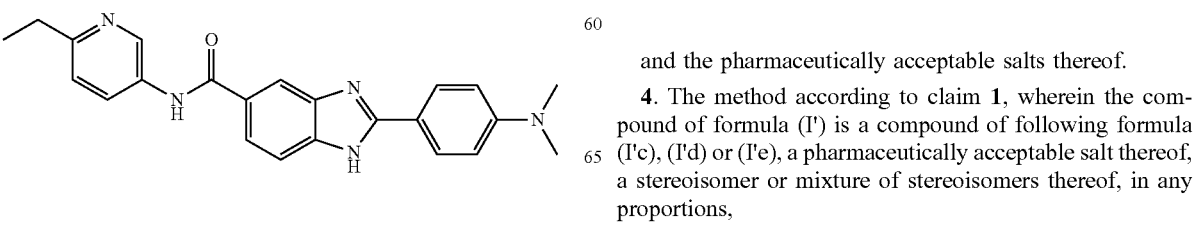

and the pharmaceutically acceptable salts thereof.

4. The method according to claim 1, wherein the compound of formula (I') is a compound of following formula (I'c), (I'd) or (I'e), a pharmaceutically acceptable salt thereof, a stereoisomer or mixture of stereoisomers thereof, in any proportions,

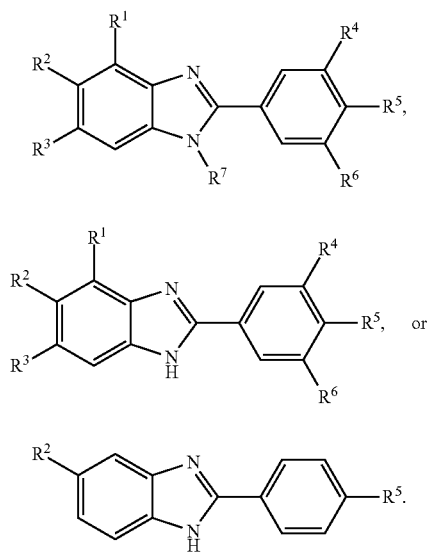

5. The method according to claim 1, wherein $R^1$, $R^3$, $R^4$, $R^6$ and $R^7$ each represent H.

6. The method according to claim 1, wherein R11 represents H or $CH_3$.

7. The method according to claim 1, wherein R12 represents an aryl, or 5- or 6-membered heteroaryl group optionally substituted with one or more groups selected from halo, (C1-C6)alkyl, OR35 and NR36R37, wherein the aryl is a phenyl and the 5- or 6-membered heteroaryl group is a furyl, thienyl, pyrrolyl, pyridyl, oxazolyl, isoxazolyl, thiazolyl, isothiazolyl, imidazolyl, pyrazolyl, oxadiazolyl, thiadiazolyl, triazolyl, tetrazolyl, pyridazinyl, pyrimidinyl, pyrazinyl, or triazinyl.

8. The method according to claim 1, wherein R21 represents H or R41 and R22 represents H or R42 with R41 and R42 representing, independently of one another, a (C1-C6)alkyl group.

9. The method according to claim 1, wherein:

R11 represents H;

R12 represents a 6-membered heteroaryl group optionally substituted with one or more groups selected from halo, (C1-C6)alkyl, OR35 and NR36R37, wherein the 6-membered heteroaryl group is a pyridyl, pyridazinyl, pyrimidinyl, pyrazinyl, or triazinyl; and R21 and R22 represent, independently of one another, H or a (C1-C6)alkyl group.

10. The method according to claim 1, wherein the compound of formula (I') is chosen from among the following compounds:

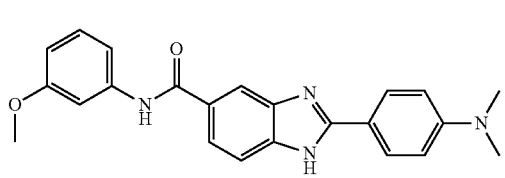

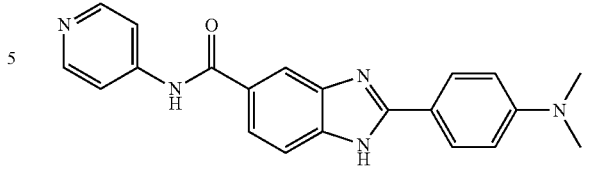

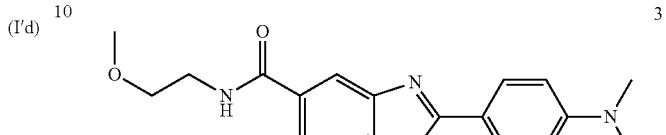

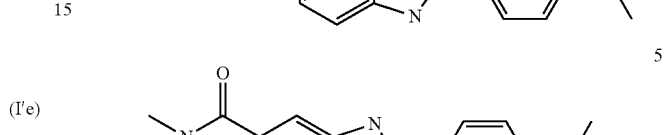

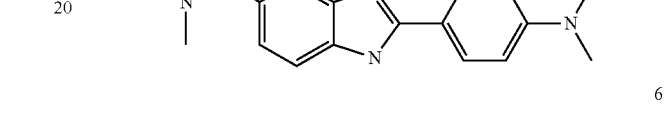

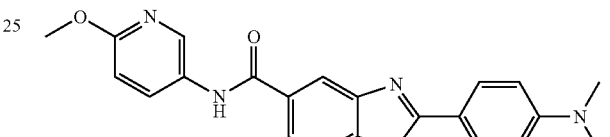

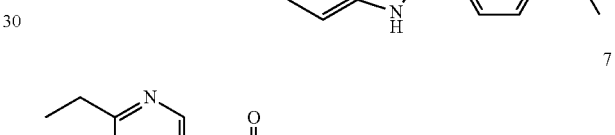

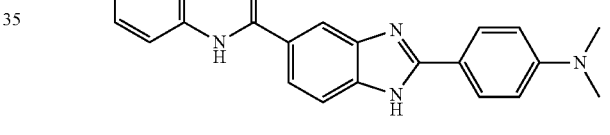

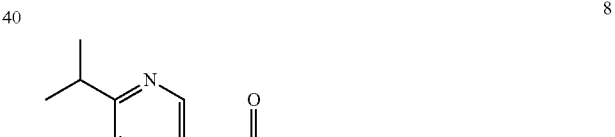

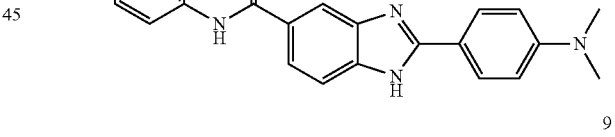

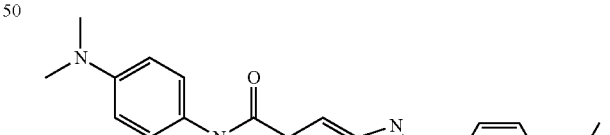

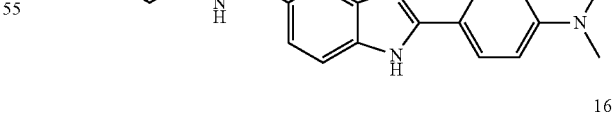

-continued

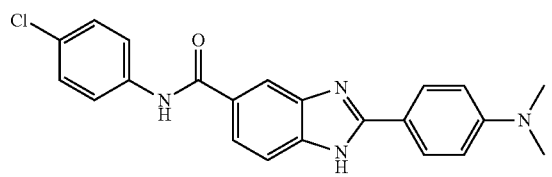

19

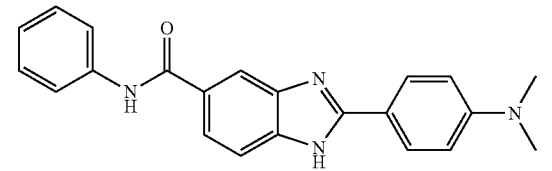 [SMILES: CN(C)c1ccc(-c2nc3cc(C(=O)Nc4ccccc4)ccc3[nH]2)cc1]

45

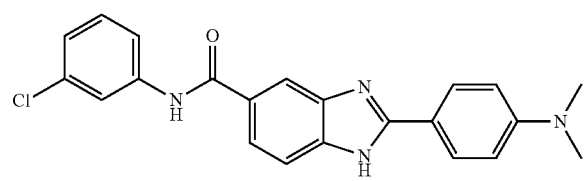 [SMILES: CN(C)c1ccc(-c2nc3cc(C(=O)Nc4cccc(Cl)c4)ccc3[nH]2)cc1]

46 and the pharmaceutically acceptable salts thereof.

11. The method according to claim 9, wherein the compound of formula (I') is chosen from among the following compounds:

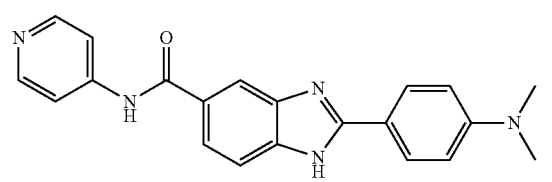

2

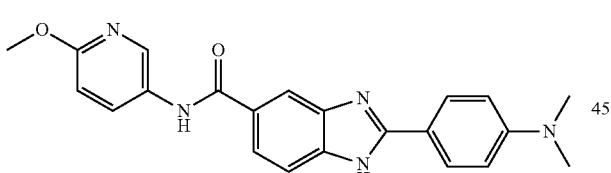

6

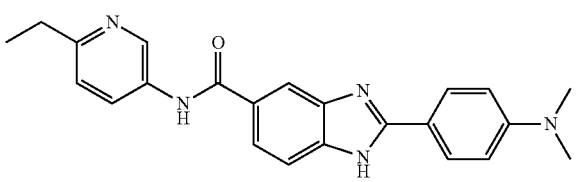

7 and the pharmaceutically acceptable salts thereof.

12. The method according to claim 1, wherein the compound of formula (I') is present in a pharmaceutical composition further comprising a pharmaceutically acceptable carrier.

13. The method according to claim 12, wherein the pharmaceutical composition further comprises another antitumour drug, as combined preparation for a simultaneous, separate or sequential administration.

14. The method according to claim 13, wherein the other antitumour drug is selected from:

abraxane, abarelix, aldesleukin, alemtuzumab, alitretinoin, allopurinol, altretamine, anastrozole, arsenic trioxide, asparaginase, azacitidine, atezolizumab, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, ipilimumab, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nivolumab, nofetumomab, oxaliplatin, paclitaxel, pamidronate, panitumumab, pegaspargase, pegfilgrastim, pembrolizumab, pemetrexed disodium, pentostatin, pipobroman, plicamycin, procarbazine, quinacrine, rasburicase, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, zoledronate, and an immune checkpoint inhibitor.

15. The method according to claim 14, wherein the immune checkpoint inhibitor is an antibody against PD1, PD-L1, or CTLA4.

* * * * *